United States Patent
Seeman et al.

(10) Patent No.: US 6,548,067 B1
(45) Date of Patent: Apr. 15, 2003

(54) ANTIGENIC CONSTRUCTS OF MAJOR HISTOCOMPATIBILITY COMPLEX CLASS I ANTIGENS WITH SPECIFIC CARRIER MOLECULES, THE PREPARATION AND USE THEREOF

(76) Inventors: Gerhard Seeman, Behringwerke Aktiengesellschaft, Postfach 11 40, D-35001 Marburg (DE); Klaus Bosslet, Behringwerke Aktiengesellschaft, Postfact 11 40, D-35001 Marburg (DE); Hans Harald Sedlacek, Behringwerke Aktiengesellschaft, Postfach 11 40, D-35001 Marburg (DE)

( * ) Notice: Subject to any disclaimer, the term of this patent is extended or adjusted under 35 U.S.C. 154(b) by 0 days.

(21) Appl. No.: 08/460,569

(22) Filed: Jun. 2, 1995

Related U.S. Application Data

(63) Continuation of application No. 07/912,677, filed on Jul. 14, 1992, now abandoned, which is a continuation of application No. 07/385,532, filed on Jul. 26, 1989, now abandoned.

(30) Foreign Application Priority Data

Jul. 28, 1988 (DE) .......................................... 38 25 615

(51) Int. Cl.[7] ...................... A61K 39/00; A61K 39/395; C07K 14/435; C07K 16/46
(52) U.S. Cl. ............................... 424/192.1; 424/133.1; 424/134.1; 424/178.1; 424/182.1; 424/193.1; 530/350; 530/387.3; 530/391.1; 530/391.7; 530/395; 530/402
(58) Field of Search ............................ 424/178.1, 182.1, 424/133.1, 134.1, 192.1, 193.1; 530/350, 387.3, 391.1, 391.7, 395, 402

(56) References Cited

U.S. PATENT DOCUMENTS

| | | | | |
|---|---|---|---|---|
| 4,478,823 A | * | 10/1984 | Sanderson | ................... 424/88 |
| 4,894,443 A | * | 1/1990 | Greenfield et al. | ......... 530/388 |
| 5,130,297 A | * | 7/1992 | Sharma et al. | |
| 5,258,498 A | * | 11/1993 | Huston et al. | |

FOREIGN PATENT DOCUMENTS

EP  0 334 300  9/1989  ......... A61K/39/395

OTHER PUBLICATIONS

Alberts et al., Molecular Biology of The Cell, 1228–35 (1994).
Liu et al Science 239: 395,1998.*
Rosenberg et al., Evidence for involvement of dual–function T cells in rejection of MHC class I disparate skin grafts. Assessment of MHC class I alloantigens as in vivo helper determinants, J. Exp. Med., 168(1):33–45 (1988) (abstract only).
Mizoguchi et al., Genetic and stimulatory cell type requirements for inducing class I major histocompatibility complex alloantigen–specific in vivo cytotoxic T cell immunity, Eur. J. Immunol., 15:487–94 (1985) (abstract only).
Brandl et al., Killing of human leukemia/lymphoma B cells by autologous T cells activated with bispecific antibodies, (1996) (abstract only).

(List continued on next page.)

*Primary Examiner*—David Saunders
(74) *Attorney, Agent, or Firm*—Finnegan, Henderson, Farabow, Garrett & Dunner, L.L.P.

(57) ABSTRACT

Antigenic constructs which result from linkage of major histocompatibility complex (MHC) class I antigens with specific carrier molecules are described. The linkage is effected N- or C-terminally by covalent bonding or, for example, in the case of non-covalent bonding by an avidin/biotin bridge. The specific carrier molecules bind selectively to target cells and are preferably monoclonal antibodies. Processes of genetic manipulation for the preparation of such constructs are indicated. Antigenic constructs according to the invention are used to damage or eliminate target cells.

10 Claims, 34 Drawing Sheets

OTHER PUBLICATIONS

Elliott et al., Allorecognition of purified major histocompatibility complex glycoproteins by cytotoxic T lymphocytes, Proc. Natl. Acad. Sci. USA, 85:2728–2732 (1988).
Sedlack, H. H. Critical Reviews in Oncogenesis 5 (6): 555–587, 1994.*
Swartz, T. J. et al. Transplantation 46: 137–143, Nov. 1988.*
Eckels, D. D. et al. Proc. Natl. Acad. Sci. USA 85: 8191–8195, Nov. 1988.*
Parham, P. et al. Nature 325: 625–628, Feb. 1987.*
Mezzanzanica, D. et al. International J. Cancer 41: 609–615, Apr. 1988.*
Mentzer, S J. et al. Arch. Surg. 123: 1280–1285, Oct. 1988.*
S.G. Nathenson et al., Ann. Rev. Immunol. 4:471–502 (1986).
J. Dausset et al., Skin allograft survival in 238 human subjects, in histo–compatibility testing, P.I. Terasaki Ed., pp 381–397 (1970).
A.–M. Frischauf et al., J. Mol. Biol. 170:827–842 (1983).
G.H.A. Seemann et al., E.M.B.O. J. 5:547–552 (1986).
T. Maniatis et al., Molecular Cloning: A Laboratory Manual, Cold Spring Harbor (1982). (Table of contents).
A.M. Maxam and W. Gilbert, Methods in Enzymology 65:449–560 (1977).
F. Sanger et al., Proc. Natl. Acad. Sci. USA 74:5463–5467 (1977).
Stratagene Bluescript Exo/Mung DNA Sequencing System: Instruction Manual.
T. Simon and K. Rajewsky, Nucl. Acids Res. 16:354 (1988).
M.S. Neuberger, E.M.B.O. J. 1373–1378 (1983).
P.T. Jones et al., Nature 321:522–525 (1986).
J.J. van Rood, Human Immunol. 17:246–249 (1986).
T.J. Elliott and H.N. Eisen, Proc. Natl. Acad. Sci. USA 85:2728–2732 (1988).
Kawamura, et al., 1986. "Enhancement of antigenic potency in vitro and . . . " J. Immunol. 136(1):58–65.*
Geysen, et al., 1985. "Small peptides induce antibodies with a sequence and . . . " PNAS 87 : 178–182.*

* cited by examiner

ANTIGENIC CONSTRUCTS OF MAJOR HISTOCOMPATIBILITY COMPLEX CLASS I ANTIGENS WITH SPECIFIC CARRIER MOLECULES, THE PREPARATION AND USE THEREOF

This application is a continuation, of application Ser. No. 07/912,677, filed Jul. 14, 1992 now abandoned; which was a continuation of Ser. No. 07/385,532, filed Jul. 26, 1989 now abandoned.

The invention relates to antigenic constructs resulting from the linkage of major histocompatibility complex (MHC) class I antigens with specific carrier molecules.

Tissue-rejection reactions are the strongest-known immune responses mediated by T cells. In individuals of the same species they are caused by allogenic differences in class I and class II MHC antigens. In organ transplants, for example, any allogenic determinants of the MHC antigens present in the donor tissue are recognized as foreign by allospecific T cells of the recipient, a T cell immune response is induced, and the rejection reaction takes place unless an immunosuppressive therapy has been initiated or such a therapy proves insufficient.

It is furthermore known that MHC class I antigens are glycoproteins which are expressed on the surface of all nucleated cells. They are composed of a heavy chain, which is encoded by MHC class I genes, and of a light chain, the $\beta_2$-microglobulin which is non-covalently associated with the heavy chain. The extracellular part of the heavy chain is folded in three domains, the first two of these domains (alpha$_1$ and alpha$_2$) exhibiting a pronounced polymorphism when the amino acid sequences of hitherto known class I MHC antigens from various individuals are compared. They assist with antigen presentation and carry the allogenic determinants. The third extracellular domain has a more conserved sequence. The association with $\beta_2$-microglobulin is essential for correct folding of the heavy chain and for the transport of the molecule to the cell surface.

Isolation and characterization of mutated MHC class I antigens in mice showed that merely a few differences in amino acids on the alpha$_1$ and alpha$_2$ domains between donor and recipient suffice to induce a rejection reaction (Nathenson et al., Ann. Rev. Immunol., 1986, 4, 471–502). It has also been shown in humans that slight differences between donor and recipient lead to rejection of a transplant (Dausset, J., Rapaport, F. T., Legrand, L., Colombani, J., Marcelli-Barge, A.: Skin allograft survival in 238 human subjects: Role of specific relationships at the four gene sites of the first and the second HL-A loci., Histocompatibility Testing (1970) pages 381–397, Terasaki P. I. (Ed.)). The task which presented itself from that said above was to utilize the specific inducibility and strength of the cellular immune response in the tissue-rejection reaction to damage or destroy selected target cells.

Figure 1:
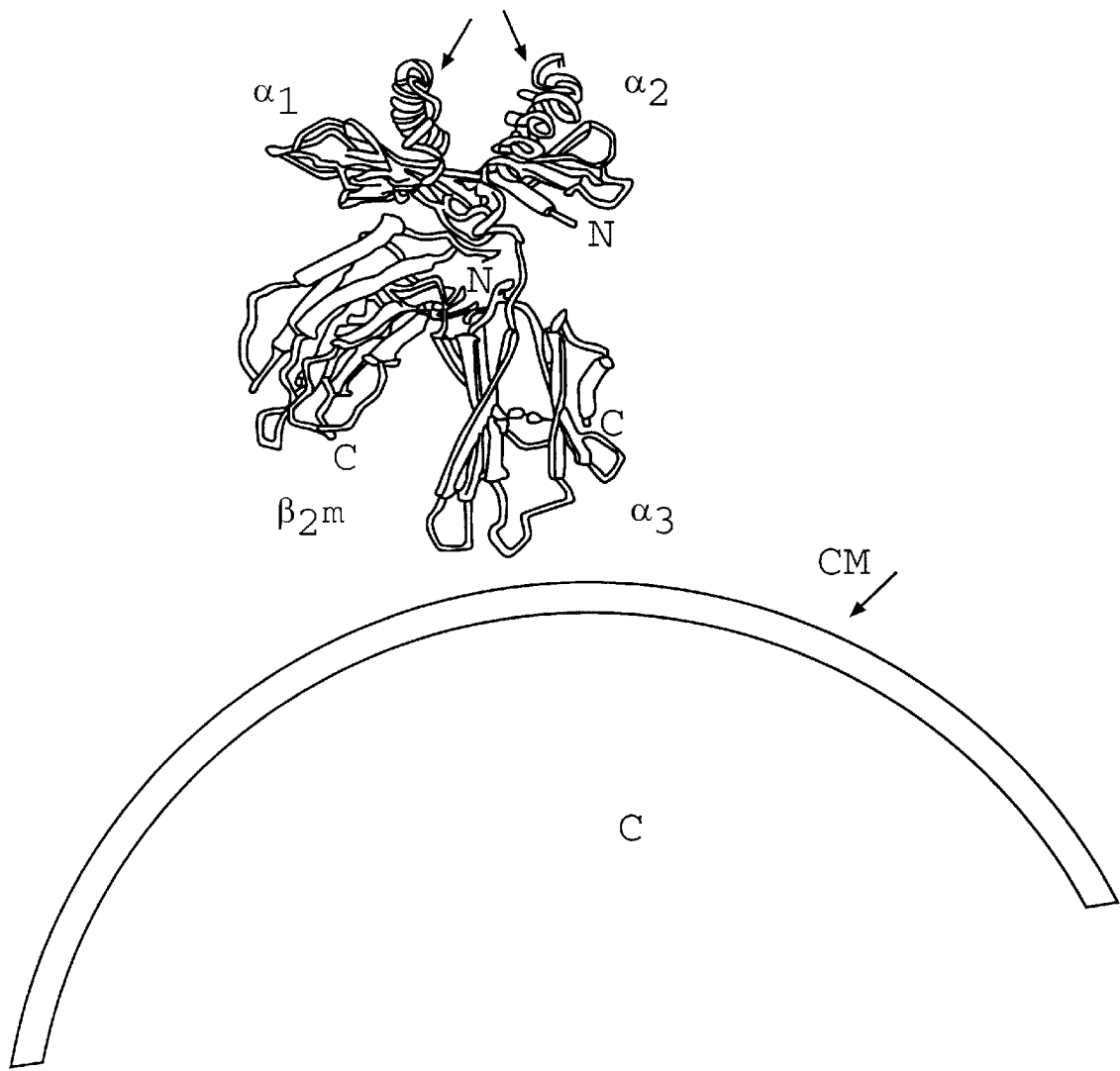
FIG. 1 shows the three domains of the class I MHC antigen chain, denoted by $\alpha_1$, $\alpha_2$, and $\alpha_3$, with arrows pointing to the alpha helices which carry the allodeterminants, "CM" representing the cell membrane, and "C" the cell.
Figure 34:
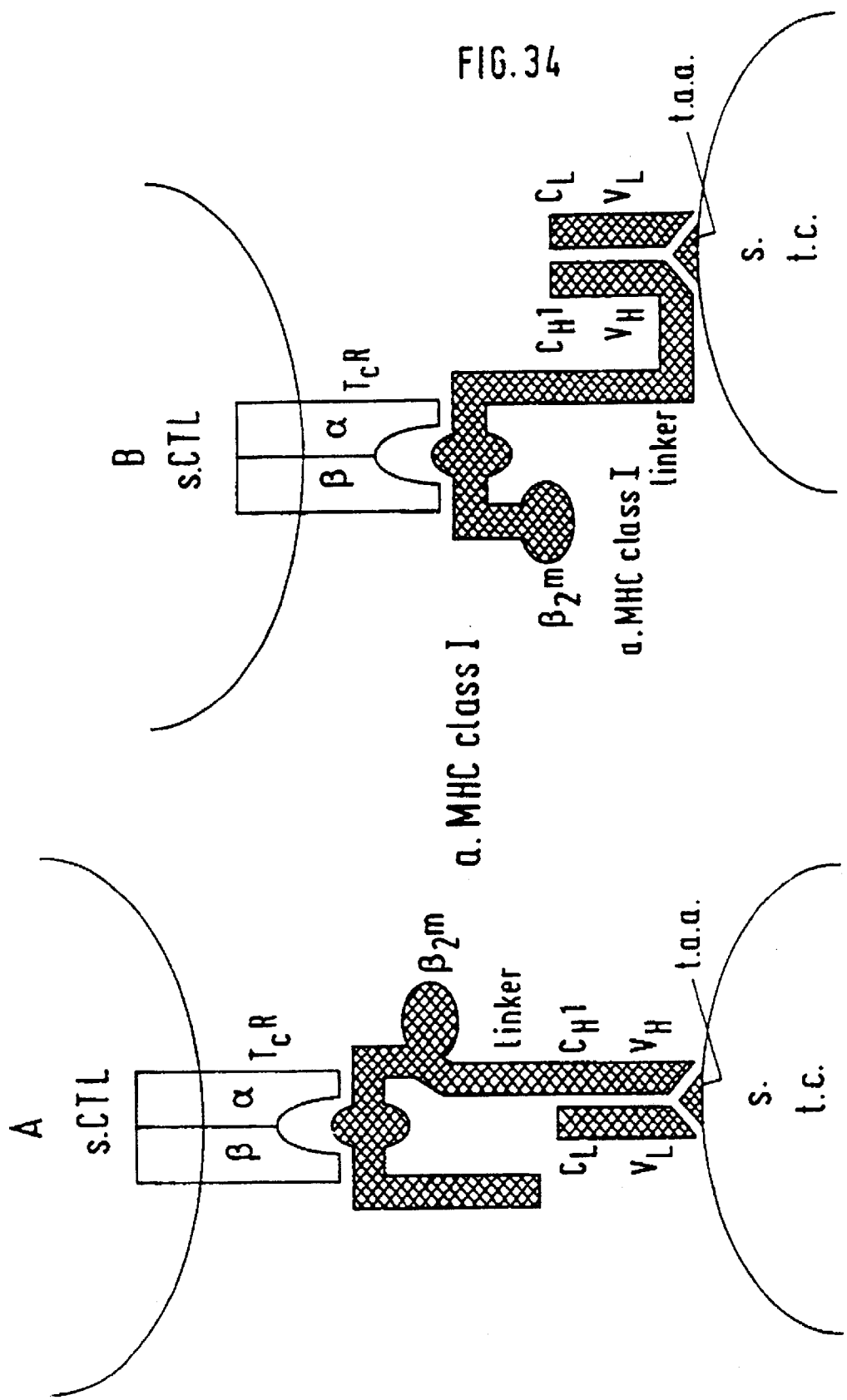
FIG. 34 shows the interaction between target cells and cytotoxic T lymphocytes mediated by antigentic constructs of MHC class I antigens and specific carrier molecules, where s.CTL denotes syngeneic cytotoxic T lymphocyte, T$_c$R denotes T-cell receptor, a.MHC class I denotes allogenic MHC class I antigen, t.a.a. denotes tumor-associated antigen, and s.t.c. denotes syngeneic tumor cell.

It has been found that target-cell-specific carriers, for example preferably monoclonal antibodies (mAb), but also polyclonal antibodies or molecules which bind to receptors on cells, can be coupled to the N- or C-terminal end of an allogenic MHC class I molecule without this altering the allogenic determinants in a disadvantageous manner. The MHC class I molecule is brought, with the aid of this target-cell-specific carrier, specifically to the target cells, which leads to activation of allospecific T cells and thus to destruction of the target cells by allospecific cytotoxic T cells. One explanation for the success of the coupling of a target-cell-specific carrier to the N- or C-terminal end of a MHC class I molecule while retaining the allogenic determinants is that the N-terminal end of the MHC class I molecule is located on the side of the alpha$_1$ and alpha$_2$ domains which points towards the cell, whereas the allogenic determinants are located on the side of the alpha$_1$ and alpha$_2$ domains which faces away from the cell (FIG. 1, FIG. 34).

Because of the great polymorphism of the MHC class I antigens in the human population, it is possible to induce a rejection reaction in almost 100% of the population with the aid of only two different MHC class I molecules selected, for example HLA B27w and HLA B27k. HLA B27w and HLA B27k are two subtypes of the serologically defined HLA B27 specificity which are defined by cytotoxic T lymphocytes. In the caucasoid population about 7% of individuals express HLA B27w and about 1% express HLA B27k. The use of, for example, both HLA B27 subtypes for the allogenization in accordance with this invention makes it possible to treat almost 100% of the caucasoid population. However, it is possible according to the invention to couple any desired MHC class I antigen to the relevant specific carriers if the abovementioned antigens do not lead in the relevant recipient to activation of allospecific T cells and subsequent damage to or destruction of the target cells. Target cells may be regarded as cells which are undesired and/or pathogenic in the body, such as, for example, tumor cells. The antigenic constructs according to the invention are accordingly suitable for tumor therapy. However, it is also possible with the MHC class I antigenic constructs according to the invention to treat other diseases which are caused by cells or the products thereof and are favorably affected by elimination of these cells. The mode of action of the hybrid molecules described in example groups I and II derives from the fact that they are able, because of the specifity of the antibody portion, to bind to an antigen on the cell. The HLA B27 portion of the fused molecule results in masking of the surface of the target cell with an allogenic MHC class I molecule. These allogenic class I molecules can then be recognized by syngeneic, allospecific, cytotoxic T cells, which leads to destruction of the target cells by the allospecific cytotoxic T cells. Accordingly, the invention relates to a) MHC class I antigens which are linked N- or C-terminally to specific carriers, the linkage preferably being brought about covalently but also possibly being non-covalent, for example by a biotin-avidin bridge, and the specific carriers binding selectively to target cells and denoting preferably monoclonal, but also polyclonal, antibodies, but being very generally receptor-binding molecules which bind to the particular cell receptors, b) a process for the preparation of the MHC class I antigenic constructs, and c) the use of the MHC class I antigenic constructs mentioned in a) and b) for damaging or eliminating target cells.

The invention is furthermore described in the examples which follow and in the patent claims, but it is not to be regarded as restricted thereto.

Examples 1–17 detailed hereinafter describe a construct according to the invention composed of the nitrophenol (NP)-specific mouse mAb B/1-8 V$_H$ gene (1), of a human IgG C F(ab')$_2$ gene (2) and of an HLA B27w gene (3). (1) and (2) are to be regarded in this context as examples of the specific carrier portion—in this case an mAb against NP—whereas (3) represents an HLA class I antigen.

The abovementioned construct is, after appropriate transformation, expressed and secreted by those myeloma cells which contain a human β$_2$-microglobulin and a light chain of an immunoglobulin and whose V gene forms with V$_H$ B/1-8 a NP binding-site, such as, for example, the mice myeloma cell J 558 L (Oi, V. T., Morrison, S. L., Herzenberg, L. A., Berg, P.: Immunoglobulin gene expression in transformed lymphoid cells. Proc. Natl. Acad. Sci. USA 80, 825, 1983). It is possible, by exchanging the V$_H$ gene of the heavy chain and using an appropriate light chain, to provide the mAb/HLA B27w fusion product with any desired specificity for which a specific or selective mAb exists.

EXAMPLES

I Examples 1 to 13 show the construction of an HLA B27/mAb fusion gene with the HLA B27 portion at the 3' end of the monoclonal antibody A) Preparation of the mAb C Gene Portion (IgG$_3$ C Gene)

Example 1

Figure 2:
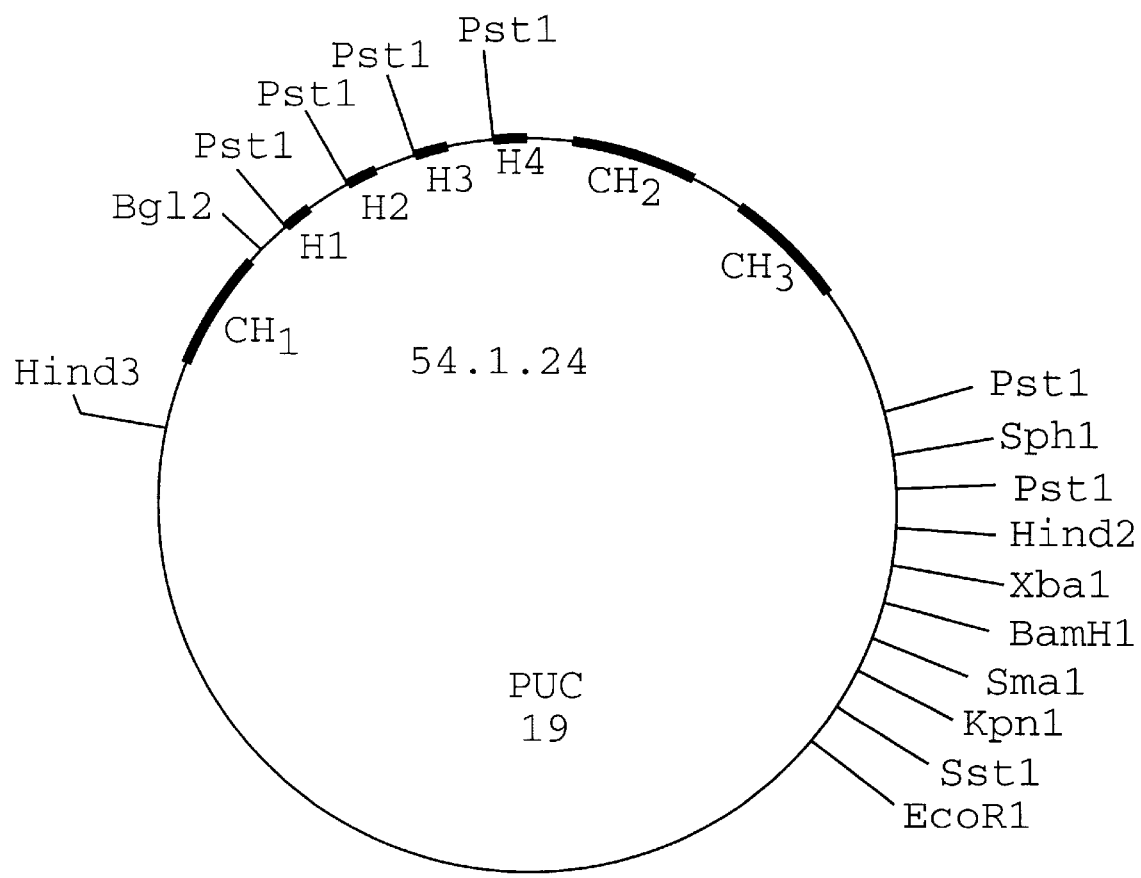
FIG. 2 shows a map of a human IgG$_3$ gene cloned into plasmid vector pUC 19 (clone 54.1.24).

A human IgG$_3$ C gene was isolated from a human gene bank in EMBL3 phages (Frischauf, A.-M., Lehrach, H., Proustka, A., Murray, N.: Lambda replacement vectors carrying polylinker sequences. J. Mol. Biol. 170, 827–842 (1983) and Seemann, G. H. A., Rein, R. S., Brown, C. S., Ploegh, H. L.: Gene conversion-like mechanisms may generate polymorphism in human class I genes. The EMBO Journal 5, 547–552 (1986)) and subcloned as a HindIII/Sph I fragment 3.1 kb in size into the plasmid vector pUC 19 (clone 54.1.24) (FIG. 2).

All the techniques used in these and in the following examples were taken, unless otherwise indicated, from Lehrach, H. and Frischauf, A.-M. Laboratory Manual EMBL (1982), Heidelberg; Maniatis, T., Fritsch, E. F., Sambrook, J.: Molecular Cloning: A laboratory manual (1982), Cold Spring Harbor Laboratory.

Example 2

Figure 3:
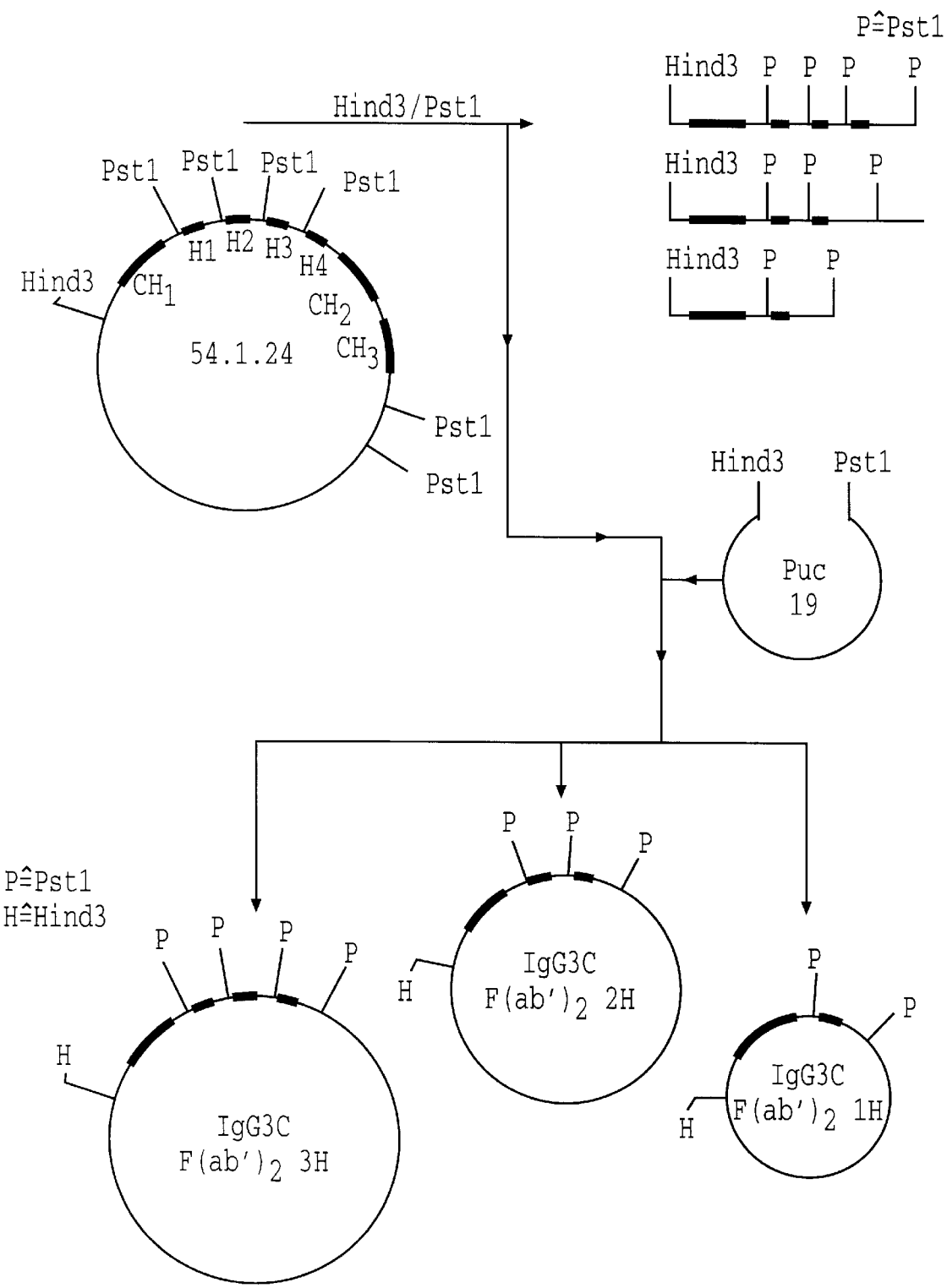
FIG. 3 diagrams the subcloning of restriction fragments from the 54.1.24 clone containing the C$_{H1}$ exon with one, two, or three hinge exons.

The 54.1.24 clone was subjected to complete HindIII and partial PstI restriction digestion. This results, inter alia, in restriction fragments which contain the $C_{H1}$ exon and one, two or three hinge exons. These fragments were cut out of an agarose gel and cloned into a pUC 19 vector cut with HindIII and PstI (FIG. 3).

Figure 4:
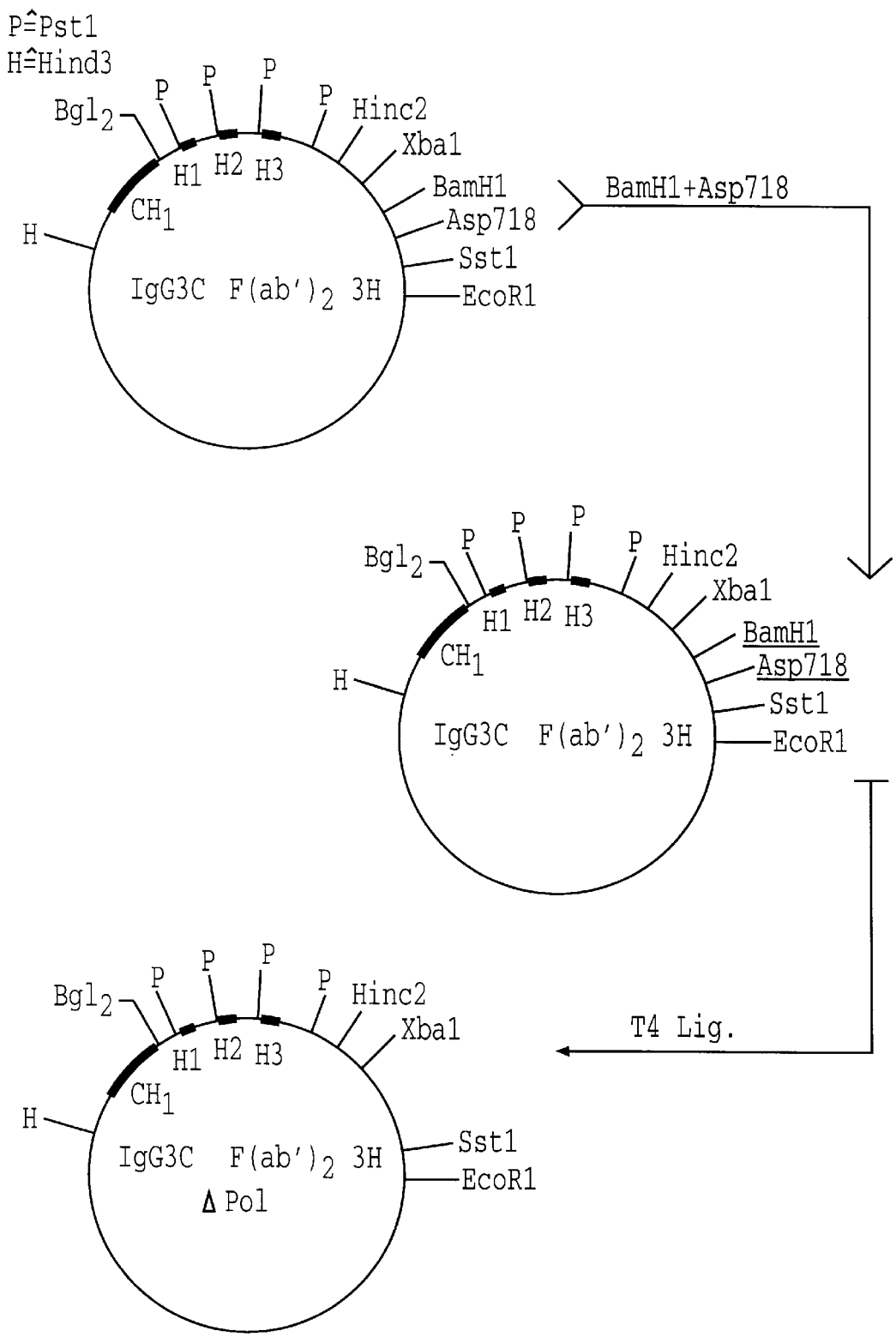
FIG. 4 diagrams deletion of the pUC 19 polylinker from the plasmid clone containing C$_{H1}$ and three hinge exons.

The plasmid clone with the $C_{H1}$ and three hinge exons (F(ab')$_2$ 3H) was then cleaved with BamHI and Asp 718, the cleavage sites were filled in and religated with $T_4$ ligase (FIG. 4). This deletes the pUC 19 polylinker between the Xba I and the SstI cleavage site.

I B) Preparation of the HLA B27 Gene

Example 3

Figure 5:
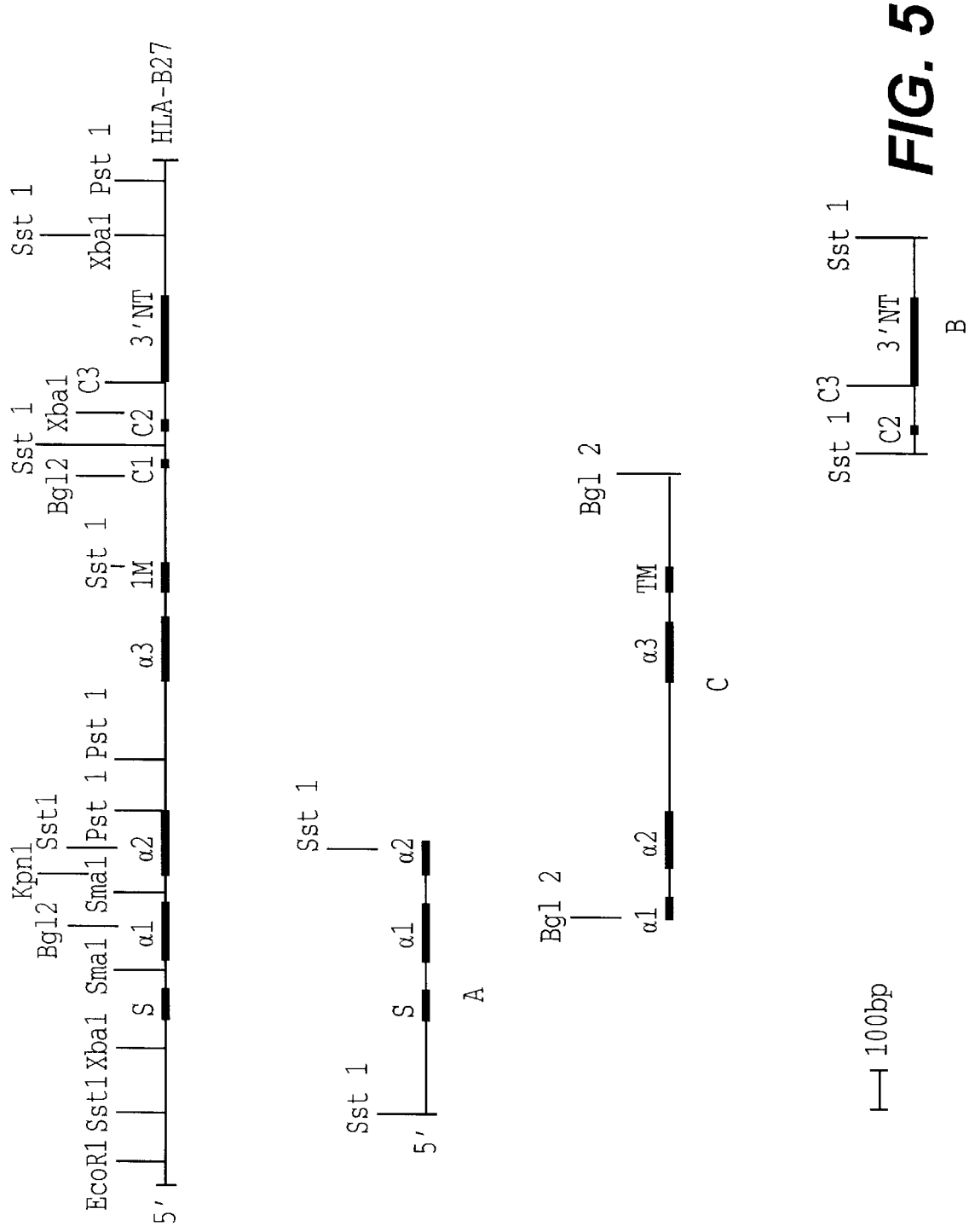
FIG. 5 shows a map of an HLA B27w gene and subfragments A, B, and C produced by SstI/BglII restriction enzyme digestion.

An HLA B27w gene was isolated from a genomic gene bank cloned in EMBL3 bacteriophages (Frischauf, A.-M., loc. cit., and Seemann, G. H. A., loc. cit.) and characterized by restriction mapping and nucleotide sequence analysis (Maxam, A., Gilbert, W.: Sequencing end-labeled DNA with base specific chemical cleavage. Meth. Enzymol. 65, 499–560 (1980) and Sanger, F., Nicklen, S., Coulson, A. R.: DNA sequencing with chain terminating inhibitors. Proc. Natl. Acad. Sci. USA 74, 5463–5471i (1977)) (FIG. 5).

The HLAA B27w gene was then digested with the restriction enzymes SstI and BglII and subcloned into the SstI and BamHI cleavage sites of pUC 19. Plasmid clones with the subfragments A, B and C (FIG. 5) were isolated.

Example 4

Figure 6:
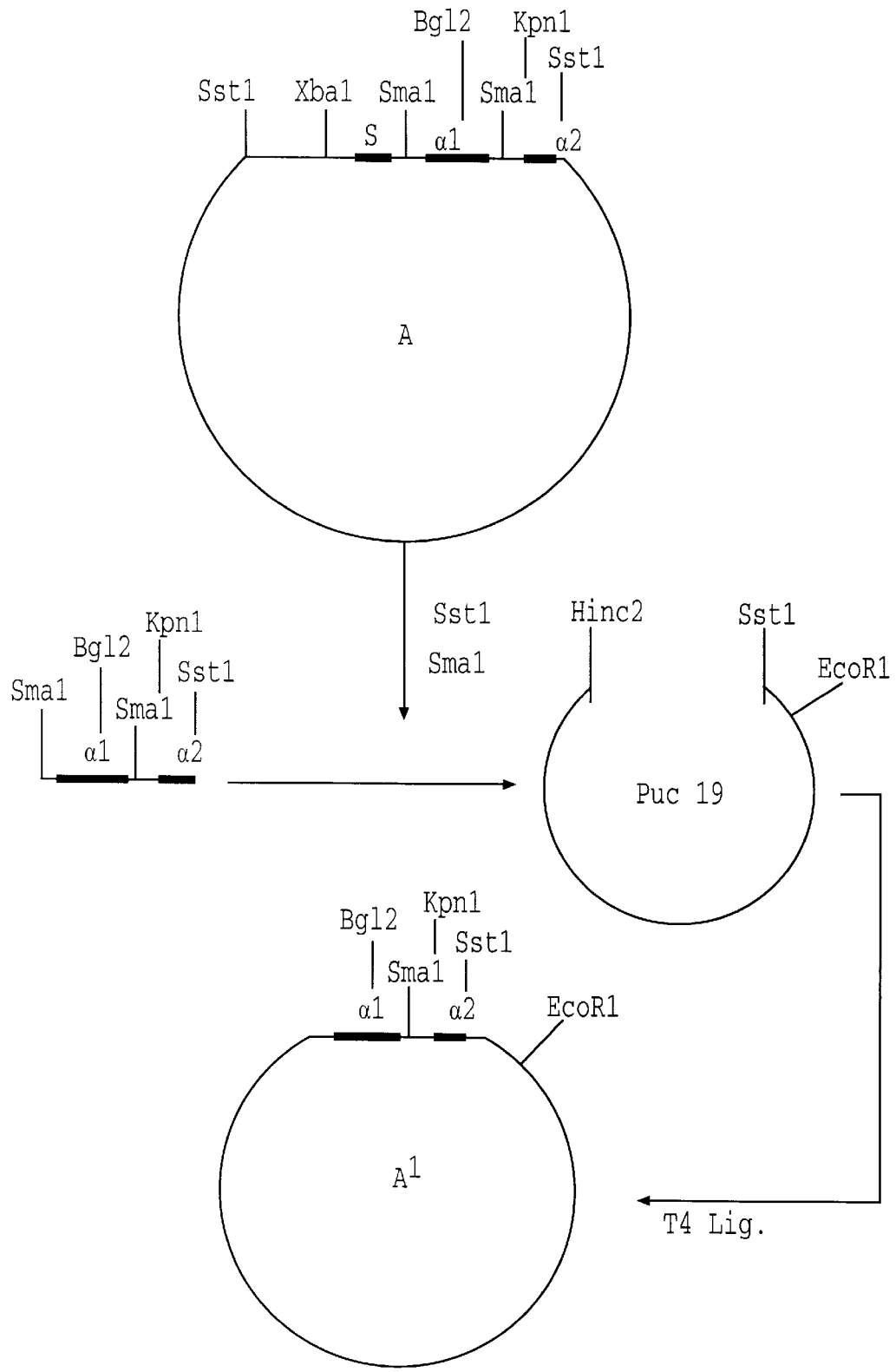
FIG. 6 diagrams cloning of fragment A' from subfragment A into pUC 19.

The plasmid with subfragment A was cleaved completely with SstI and partially with SmaI and, after fractionation on an agarose gel, the fragment A' (FIG. 6) was cloned in a pUC 19 plasmid cleaved with HincII and SstI.

Example 5

Figure 7:
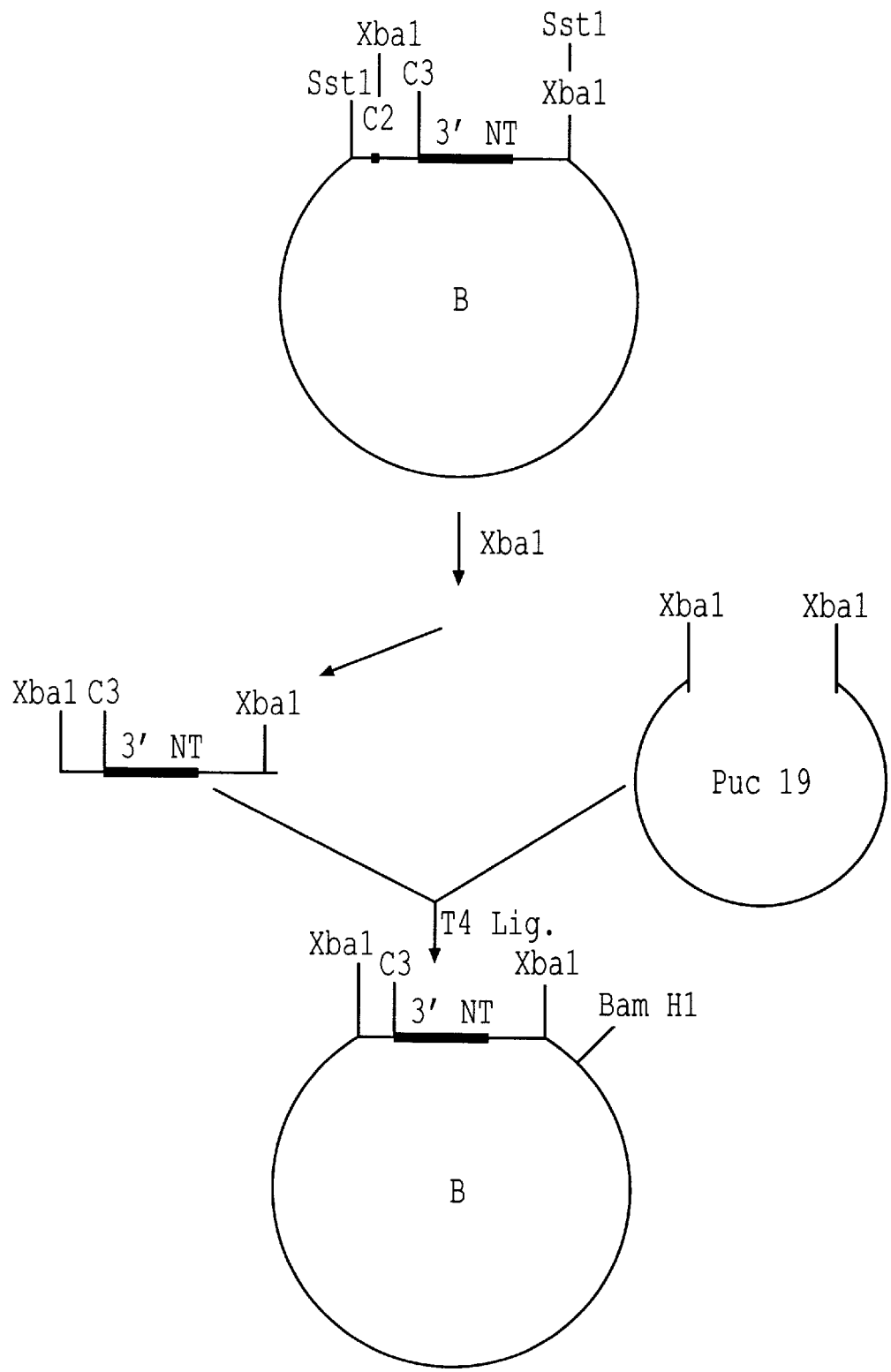
FIG. 7 diagrams cloning of fragment B' from subfragment B into pUC 19.

The plasmid with the subfragment B was digested with XbaI, and the resulting XbaI insert (B') was cloned in a XbaI-cleaved pUC 19 plasmid (FIG. 7).

Example 6

Figure 8:
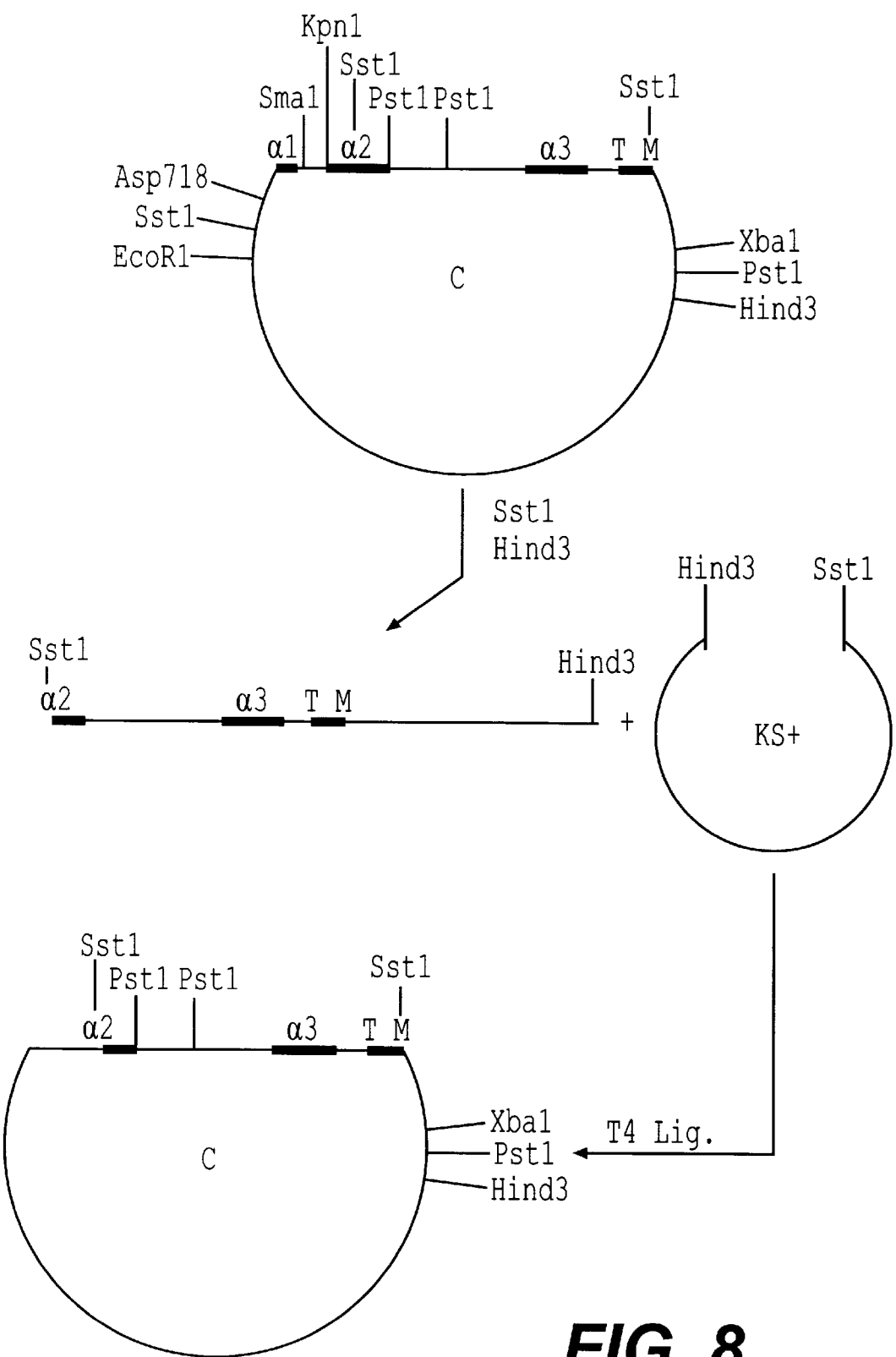
FIG. 8. diagrams cloning of fragment C' from subfragment C into the Bluescript KS$^+$ phasmid vector.

The plasmid with the subfragment C was cleaved completely with HindIII and partially with SstI, and the fragment which, in the HLA B27w gene, is attached to fragment A (C') was, after fractionation on an agarose gel, isolated and cloned into the Bluescript KS+ phasmid vector (Stratagene, LaJolla, Calif., USA) cleaved with HindIII and SstI (FIG. 8).

Example 7

Figure 9:
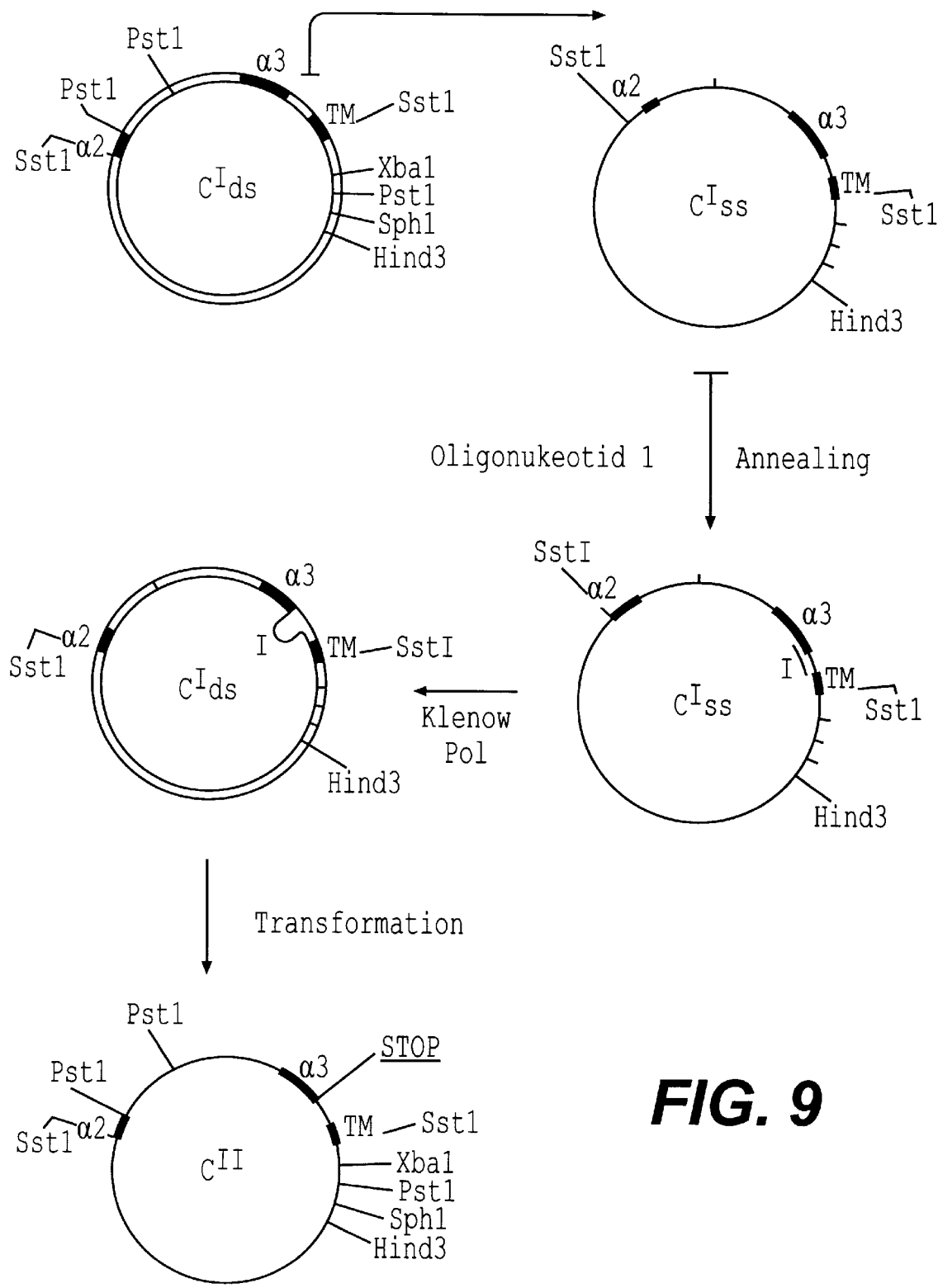
FIG. 9 diagrams introduction of a stop codon at the 3' end of the α3 exon (clone C'').

Single-stranded phages were prepared from the KS+ phasmid vector C' by infection with VCS-M13 helper phages (Stratagene, Cat # 200251) and were purified (Stratagene: Bluescript Exo/Mung DNA sequencing system: Instruction Manual). A synthetic oligonucleotide (I=5'CCTTACCTCATCTCAGG3') was hybridized onto these single strands, and the remainder of the second strand was synthesized using Klenow polymerase. The double-stranded phasmids generated in this way were transformed into XL Blue bacteria and then single-stranded phages were again generated from the resulting plasmid clones by infection with helper phages, and the nucleotide sequence was determined with the aid of an oligonucleotide primer II (5'TGAGGGCTCCTGCTT3') (Sanger, F. et al., loc. cit.). A clone in which the codon TGG (amino acid 274) at the 3' end of the alpha3 exon had been mutated to a stop codon (TGA) was identified (C'') (FIG. 9).

Example 8

Figure 10:
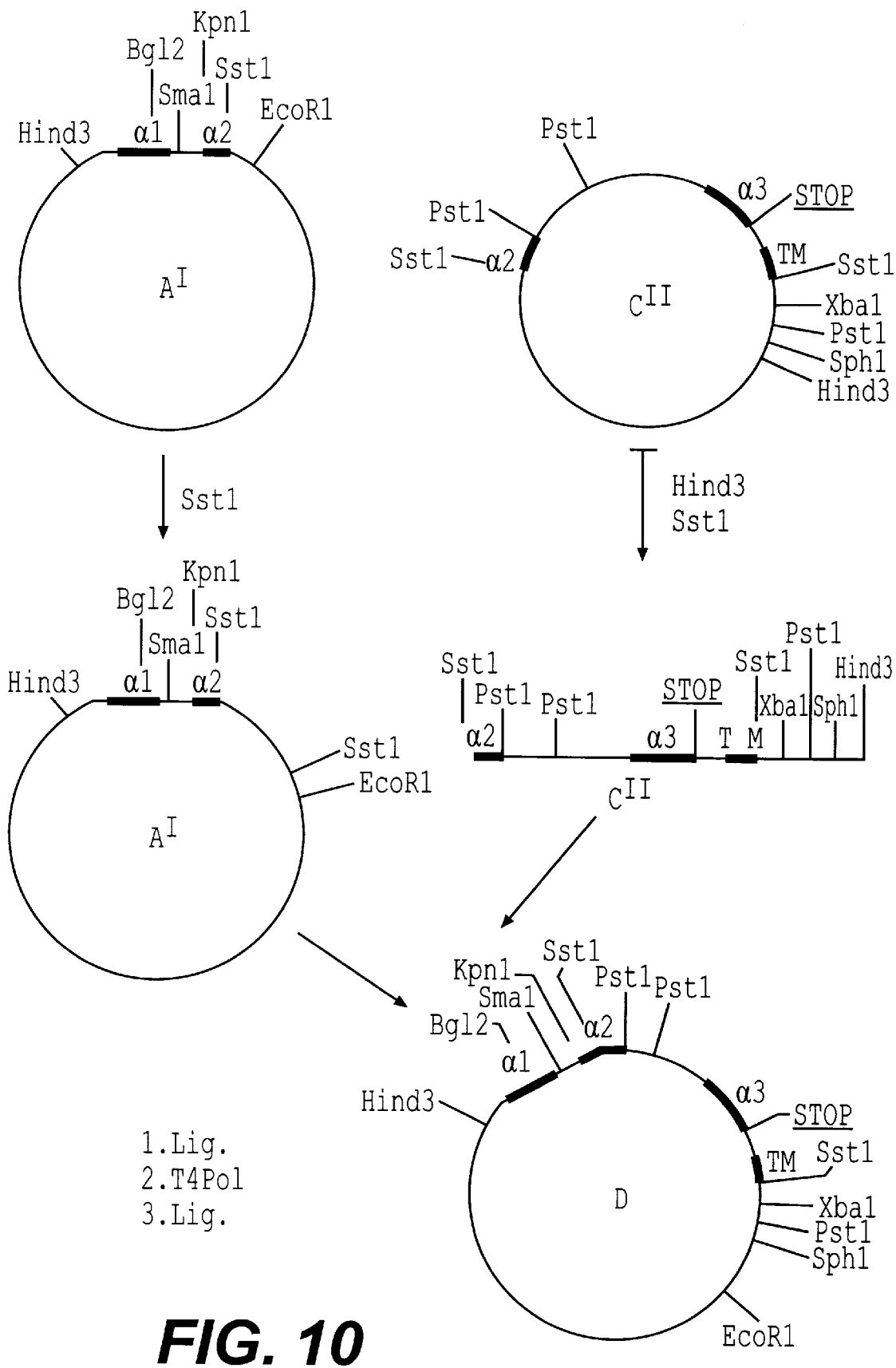
FIG. 10 diagrams ligation of the C'' fragment with the A' fragment via the SstI cleavage site in the α2 exon to yield plasmid D.

The plasmid with the fragment A' was cleaved with SstI and ligated with the C'' fragment which had been generated by a complete HindIII and partial SstI cleavage of the phasmid clone C'' and had been isolated after fractionation on an agarose gel. After ligation at 14° C. for 30 minutes, the unligated ends were filled in with $T_4$ polymerase and subsequently ligated once again. Restriction mapping was used to identify the plasmid D (FIG. 10) in which the fragment A' is connected to the fragment C'' via the SstI cleavage site in the alpha2 exon.

Example 9

Figure 11:
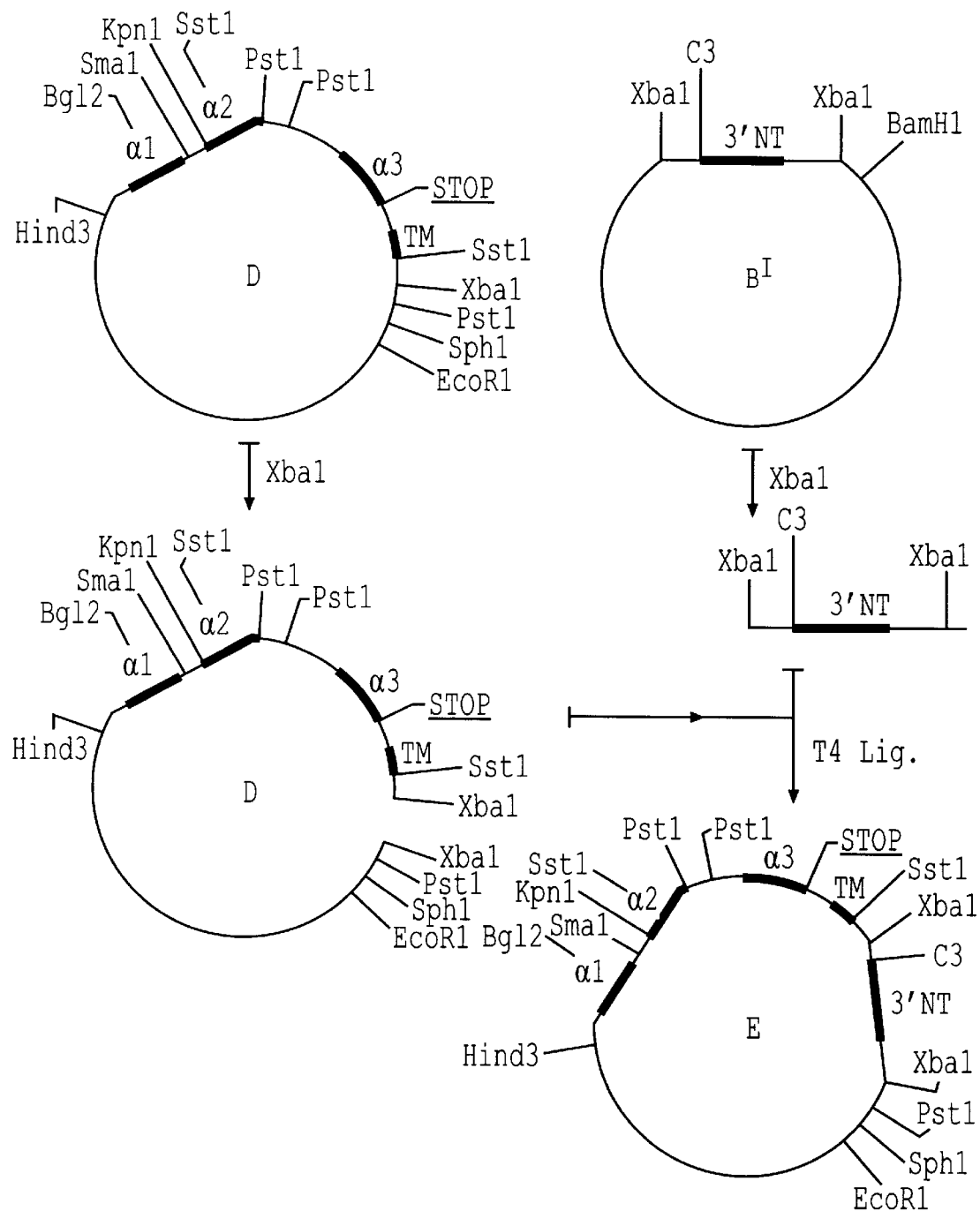
FIG. 11 diagrams ligation of the B' fragment with the D fragment to yield plasmid E.

The plasmid with the fragment D was cleaved with XbaI and ligated with the fragment B' which had been cut out of the plasmid B' with XbaI and had been purified after fractionation on an agarose gel (FIG. 11). Nucleotide sequence analyses (17) were used to identify a plasmid (E) in which the B' fragment is ligated in the correct 5'-3' orientation to the fragment D.

C) Fusion of the Modified HLA B27w Gene with the IgG3 C F(ab')$_2$ 3H Gene Fragment Example 10

Figure 12:
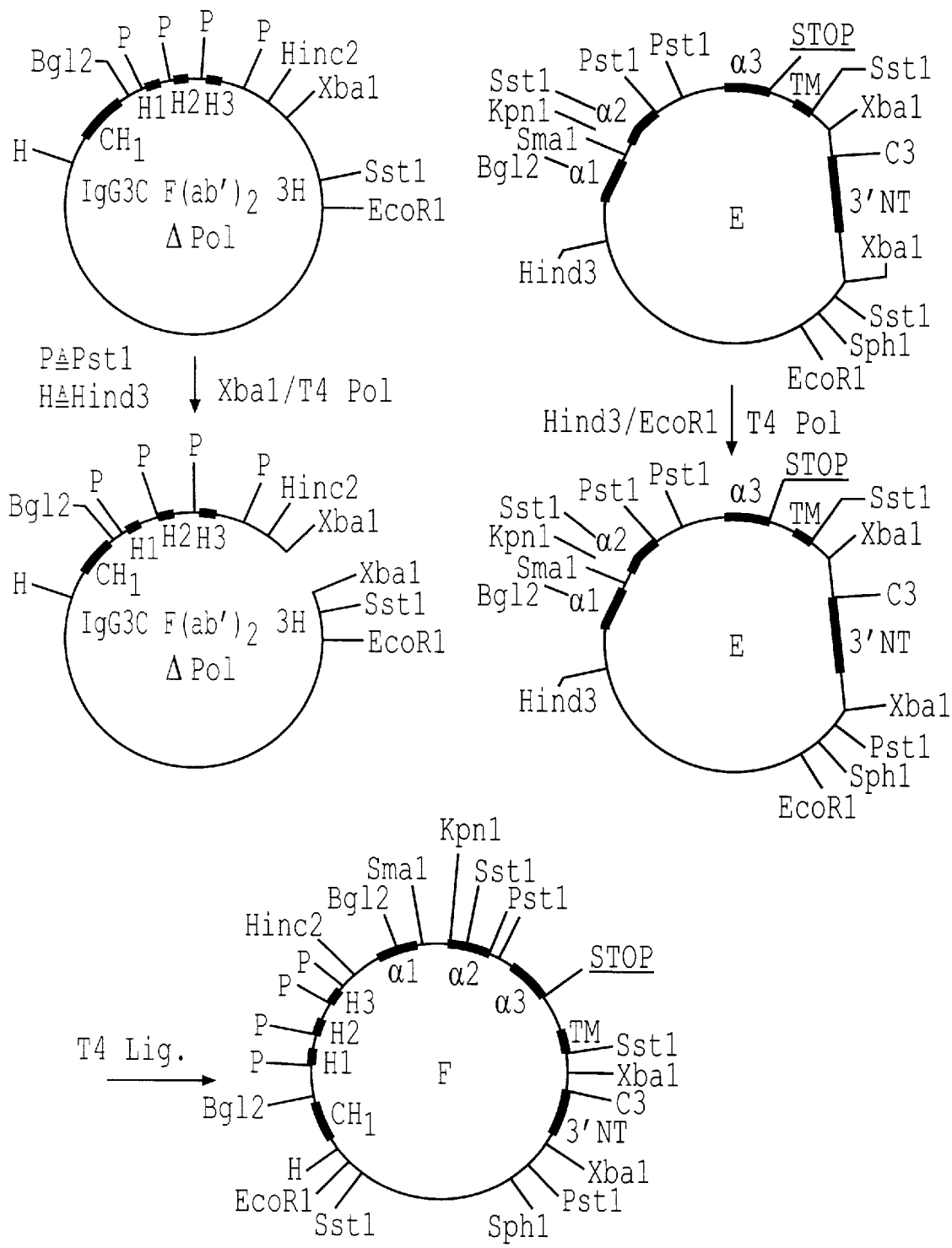
FIG. 12 diagrams construction of plasmid F, in which the modified HLA B27w gene is fused in the correct 5'-3' orientation to the F(ab')$_2$ 3H gene.

The fragment E was cut out of the plasmid E by cleavage with EcoRI and HindIII, the ends were filled in with $T_4$ polymerase and purified after fractionation on an agarose gel. This purified fragment E was then ligated with the plasmid which contains the IgG3 F(ab')$_2$ 3H fragment after the latter had been cleaved and the XbaI ends had been filled in with $T_4$ polymerase (FIG. 12). Restriction mapping was used to identify the clone which contained the plasmid F, in which the modified HLA B27w gene is fused in the correct 5'-3' orientation to the F(ab')$_2$ 3H gene.

Example 11

Figure 13:
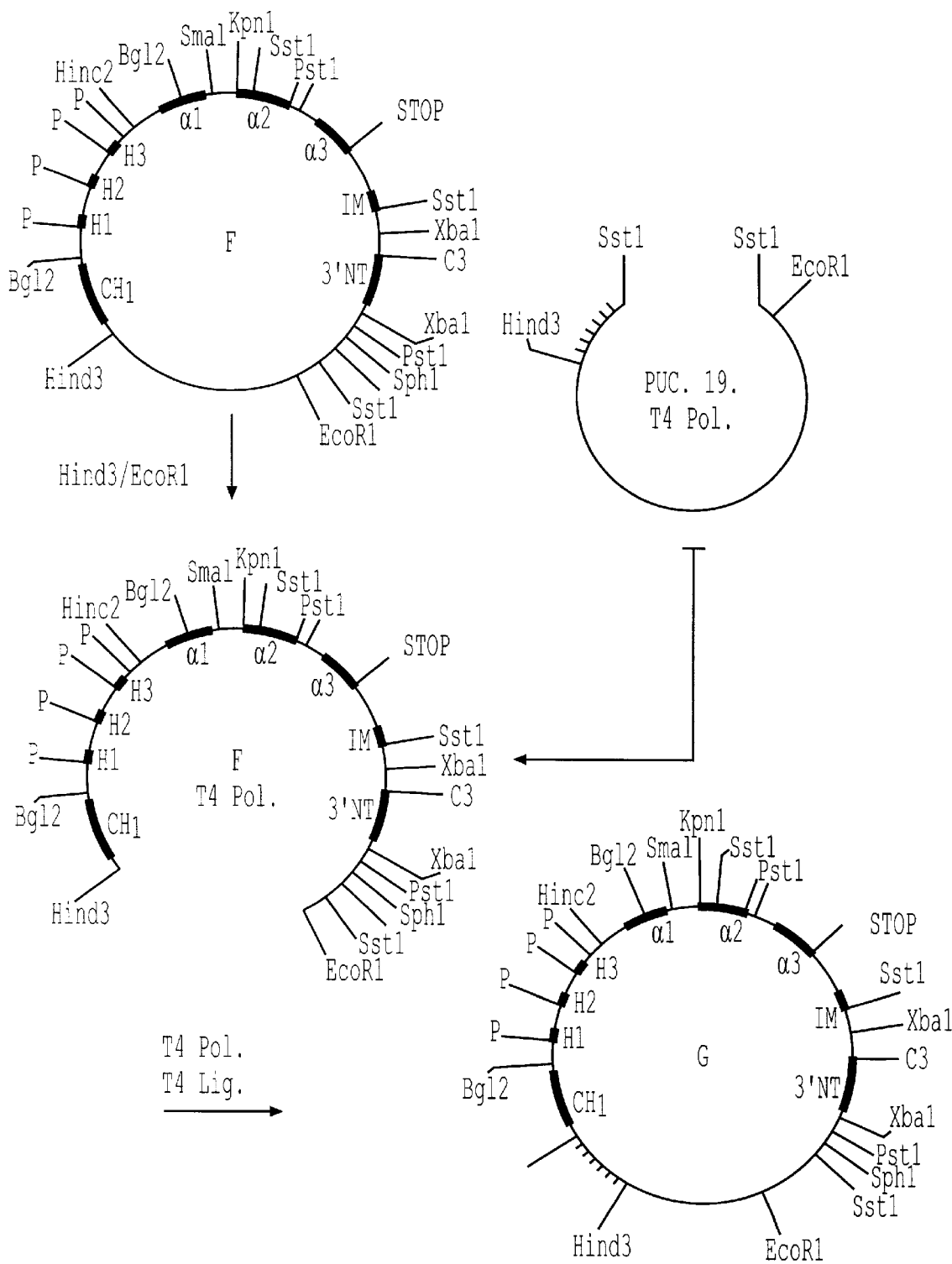
FIG. 13 diagrams insertion of a polylinker in front of the 5' end of the fragment F to yield plasmid G.

The fragment F was cut out with HindIII and EcoRI in order to place a polylinker in front of the 5' end of the fragment F. The HindIII and XbaI ends were filled in with $T_4$ polymerase and cloned into a pUC 19 which had been cleaved with SstI and whose SstI ends had been filled in with $T_4$ polymerase. Restriction analyses were used to identify the clone with the plasmid G which has the pUC 19 polylinker 5' from the fragment F (FIG. 13).

Example 12

Figure 14:
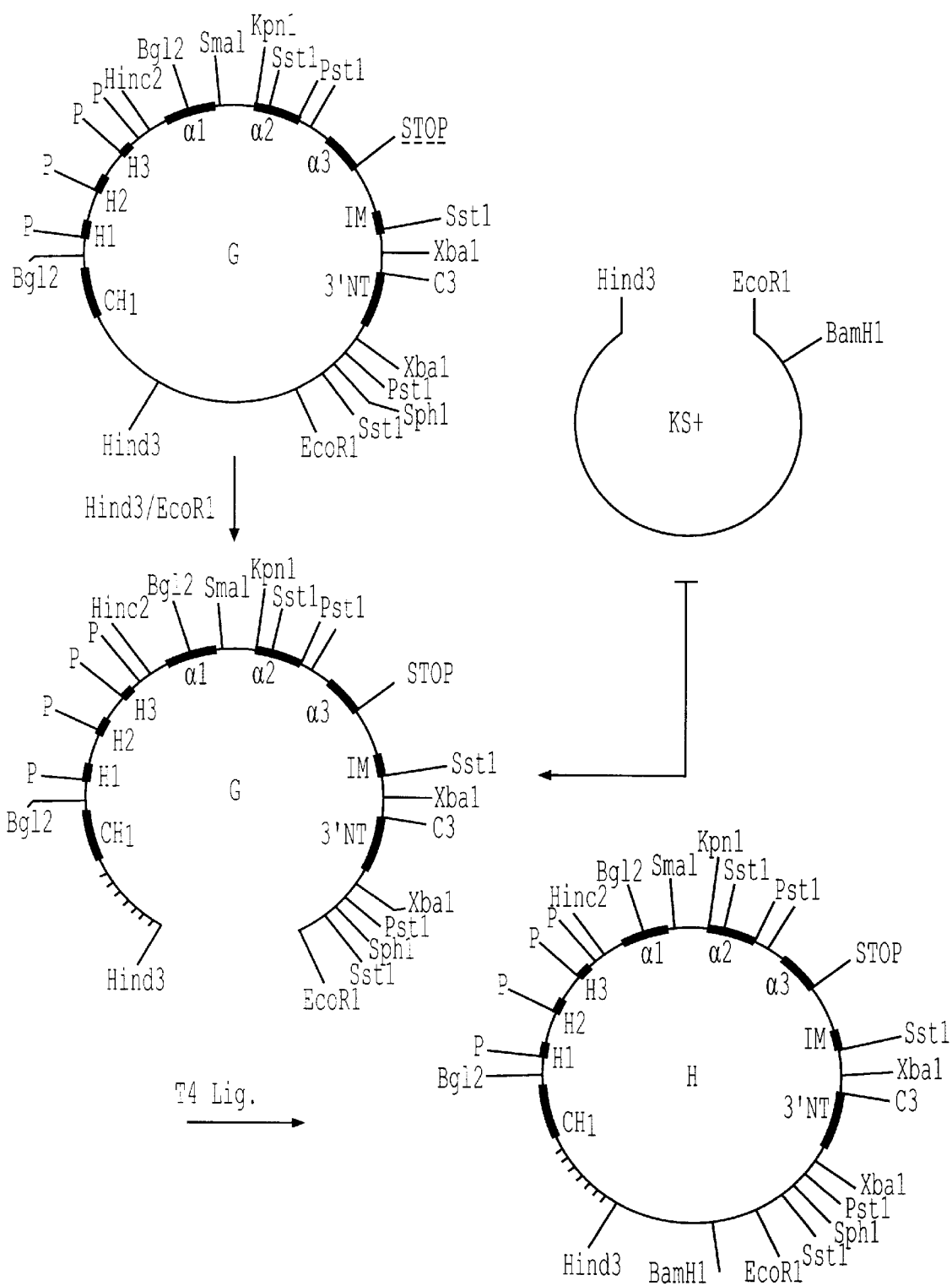
FIG. 14 diagrams cloning of the fragment from plasmid G with the IgG F(ab')$_2$HLA B27w fusion gene into the Bluescript KS$^+$ phasmid vector to yield plasmid H.

The plasmid G was cleaved with HindIII and EcoRI, and the insert with the IgG F(ab')$_2$ HLA B27w fusion gene was isolated and cloned into a Bluescript KS+ phasmid vector (Stratagene: Bluescript Exo/Mung DNA sequencing system: Instruction Manual) cleaved with HindIII and EcoRI (FIG. 14).

Example 13

Figure 15:
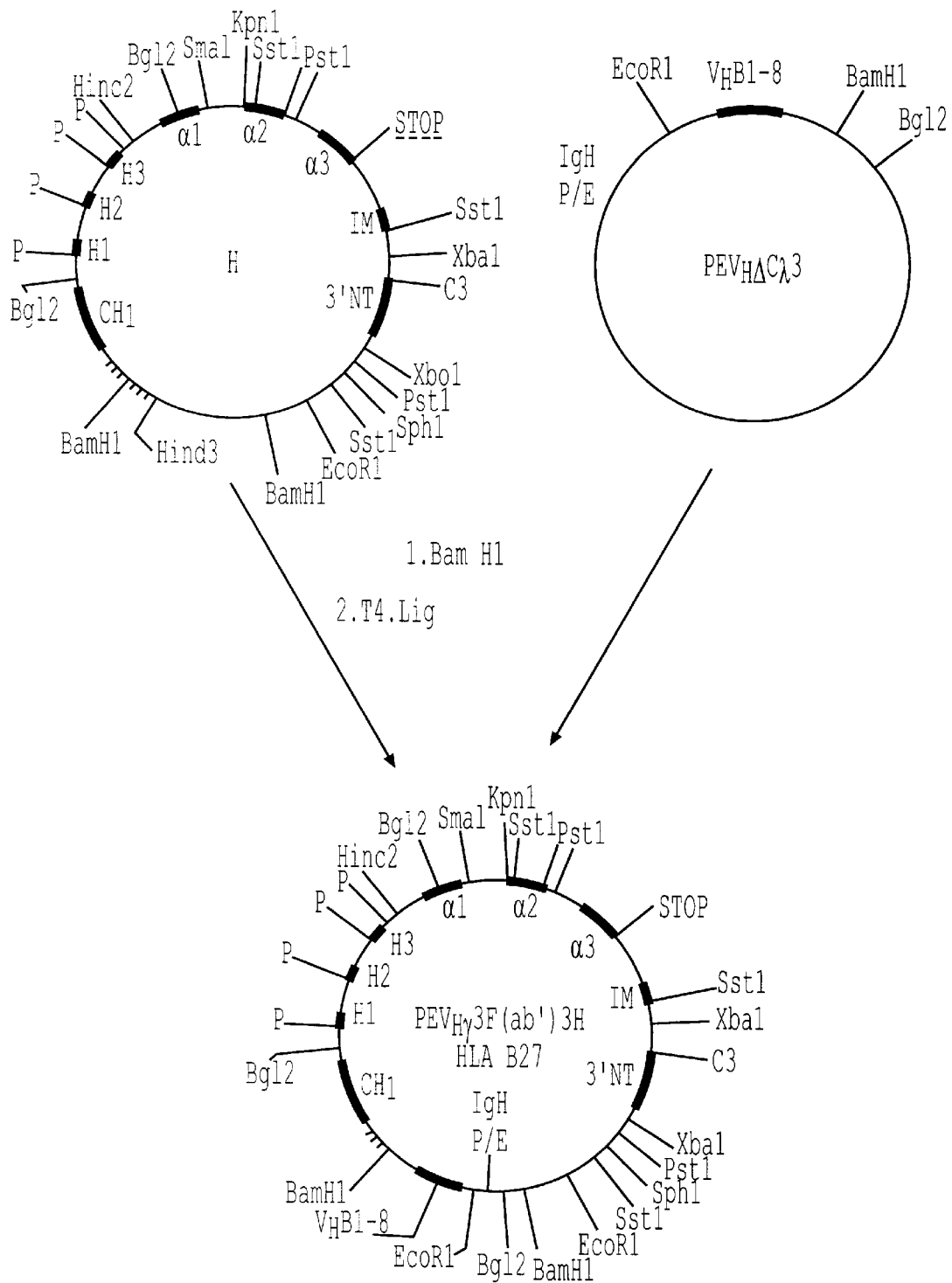
FIG. 15 diagrams cloning of a BamHI fragment from plasmid H into eukaryotic expression vector PEV$_H$ to yield plasmid I.

The plasmid H resulting from this cloning was then cleaved with BamHI, and the insert was cloned into the eukaryotic expression vector pEV$_H$ (Simon, T., Rajewsky, K., Nucl. Acids Res. 16, 354, (1988), which contains the IgG H promoter/enhancer sequences and the V$_H$ gene originating from the NP-specific mouse mAb B/1-8 which had been cleaved with BamHI (FIG. 15) (Neuberger, M. N.: EMBO Journal 2, 1375–1378 (1983)). Restriction analysis was used to identify the plasmid I in which the IgG 3 F(ab')$_2$ HLA B27w fusion gene is cloned in the correct 5'-3' orientation behind the V$_H$ gene.

The mAb/HLA B27w fusion gene now possesses intact 5' and 3' ends having all the signals required for expression in eukaryotic cells. The construct is, as stated in the introduction, expressed and secreted in every myeloma cell which contains a human $\beta_2$-microglobulin and a light chain of an immunoglobulin and whose V gene forms with $V_H$ B/1-8 a NP binding site, such as, for example, the mouse myeloma cell J 558L (Oi, V. T., Morrison, S. L., Herzenberg, L. A., Berg, P., Proc. Natl. Acad. Sci. USA 80, 825 (1983)).

II Examples 14 to 17 show the construction of an HLA B27/mAb fusion gene with the HLA B27 portion at the 5' end of the monoclonal antibody A) Preparation of the HLA B27 Gene

Example 14

An HLA B27w gene was isolated from a genomic gene bank cloned in EMBL3 bacteriophages (Frischauf et al., loc. cit. and Seemann, G. H. A., loc. cit.) and characterized by restriction mapping and nucleotide sequence analysis (Maxam et al., loc. cit. and Sanger et al., loc. cit.) (FIG. 5).

The HLA B27w gene was then digested with the restriction enzymes SstI and BglII and subcloned into the SstI and BamHI cleavage sites of pUC 19. Plasmid clones with the subfragments A, B and C (FIG. 5) were isolated.

Figure 16:
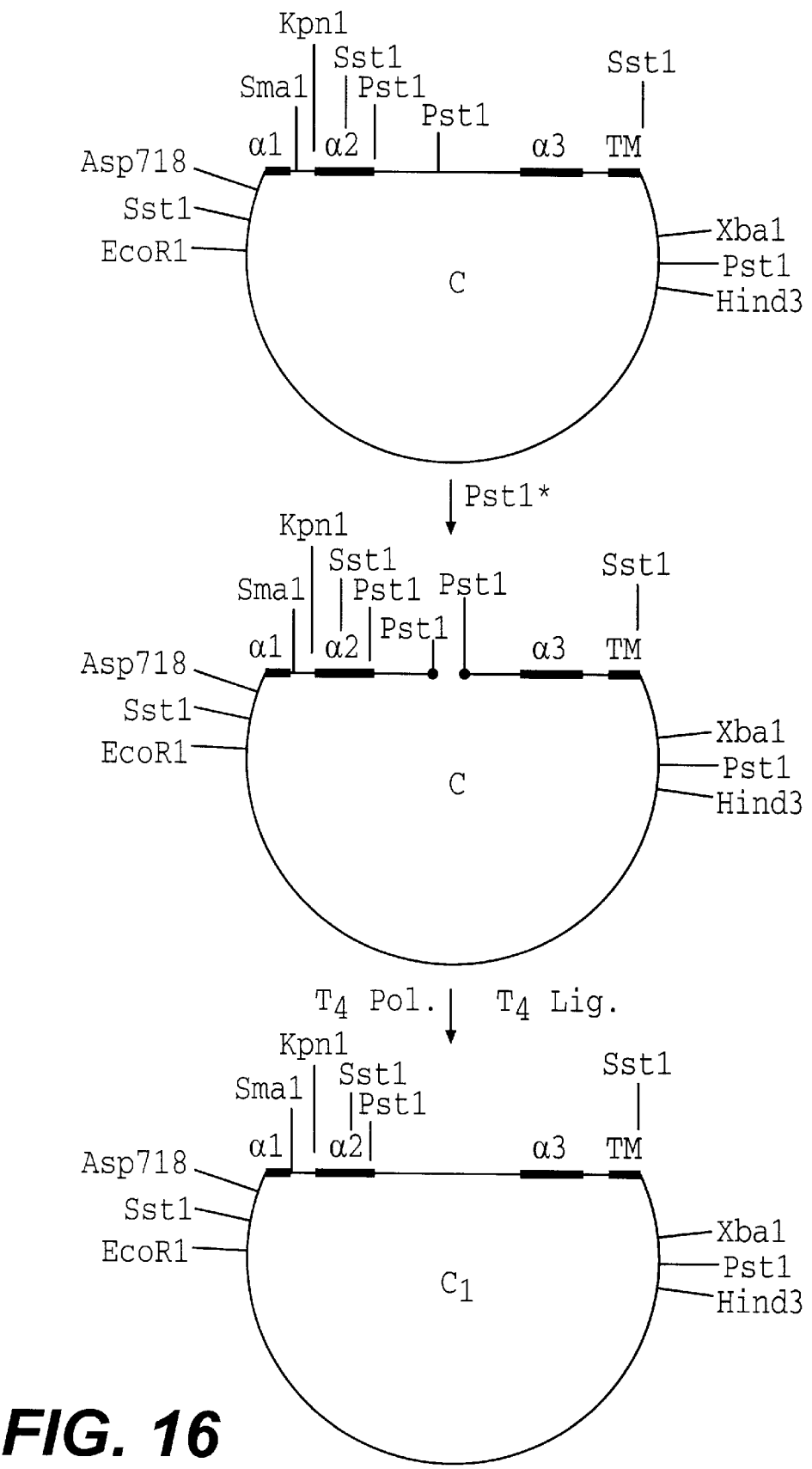
FIG. 16 diagrams removal of a PstI site from the HLA B27 subclone C to yield plasmid clone C1.

The plasmid with the HLA B27 subclone C was partially cleaved with PstI. The protruding 3' ends of the PstI cleavage sites were removed with $T_4$ polymerase, with addition of dGTP, and religated with $T_4$ ligase. Restriction analysis was used to identify the plasmid clone C1 which contains no PstI cleavage site in the intron between the alpha2 and alpha3 exon (FIG. 16).

Figure 17:
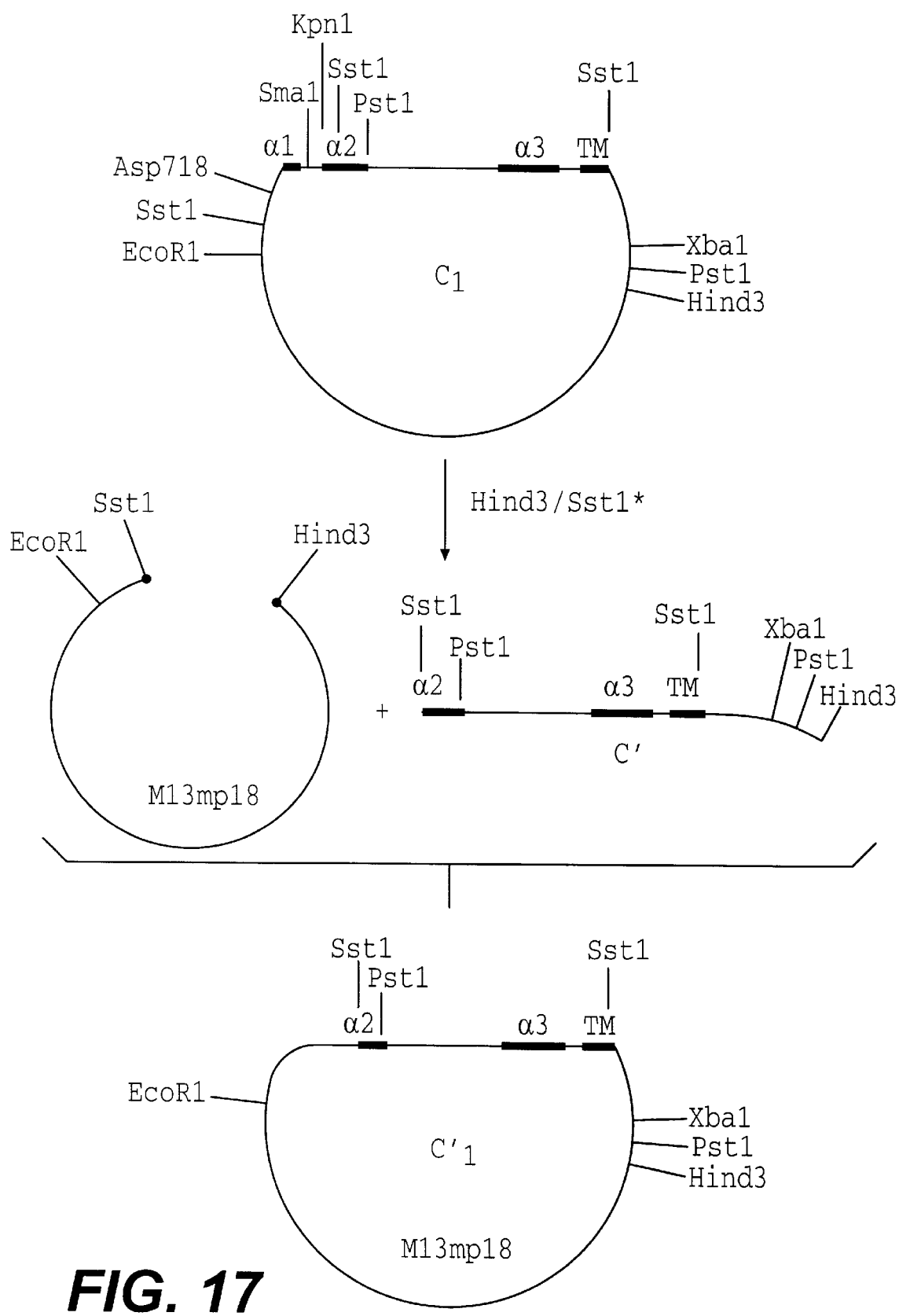
FIG. 17 diagrams isolation and subcloning of fragment C1' from plasmid C1 into vector M13 mp18.

The plasmid clone C1 was cleaved partially with SstI and completely with HindIII, and the C1' fragment was isolated and cloned into a double-stranded M13 mp18 vector cleaved with SstI and HindIII. The M13 clone C1' with the C1' fragment was identified by determining the nucleic acid sequence of the insert (FIG. 17).

Using the protocol of the Bio-Rad Muta-Gene M13 mutagenesis kit there were isolated from the C1' M13 mp18 phages in the bacterial strain CJ236 single-stranded phages which contained uracils. An oligonucleotide (oligonucleotide III) with the sequence 5' GCGCGCTG-GAGCGTCTC3' was hybridized onto these single-stranded phages and the second strand was synthesized with addition of $T_4$ polymerase, DNTP and $T_4$ ligase.

Figure 18:
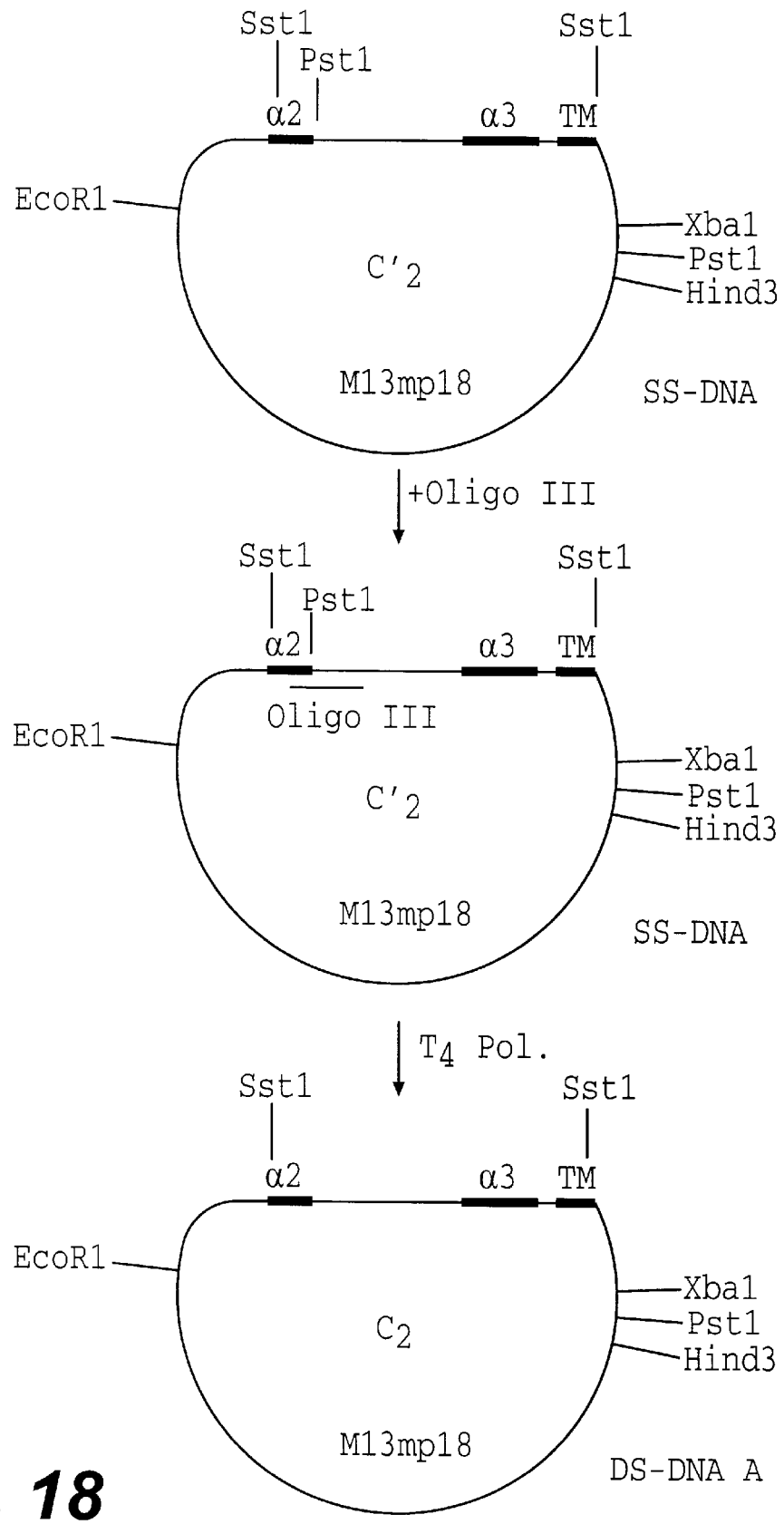
FIG. 18 diagrams destruction of the PstI restriction cleavage site in the α2 exon of clone C'$_1$ to yield clone C$_2$.

After infection of the bacterial strain MV 1190 the mutated clone C2 was identified by restriction analysis of the M13 mp18 double-stranded DNAs and confirmed by nucleic acid sequence analysis (FIG. 18). The mutagenesis resulted in destruction of the PstI restriction cleavage site in the alpha2 exon without altering the reading frame or the encoded amino acid sequence.

Figure 19:
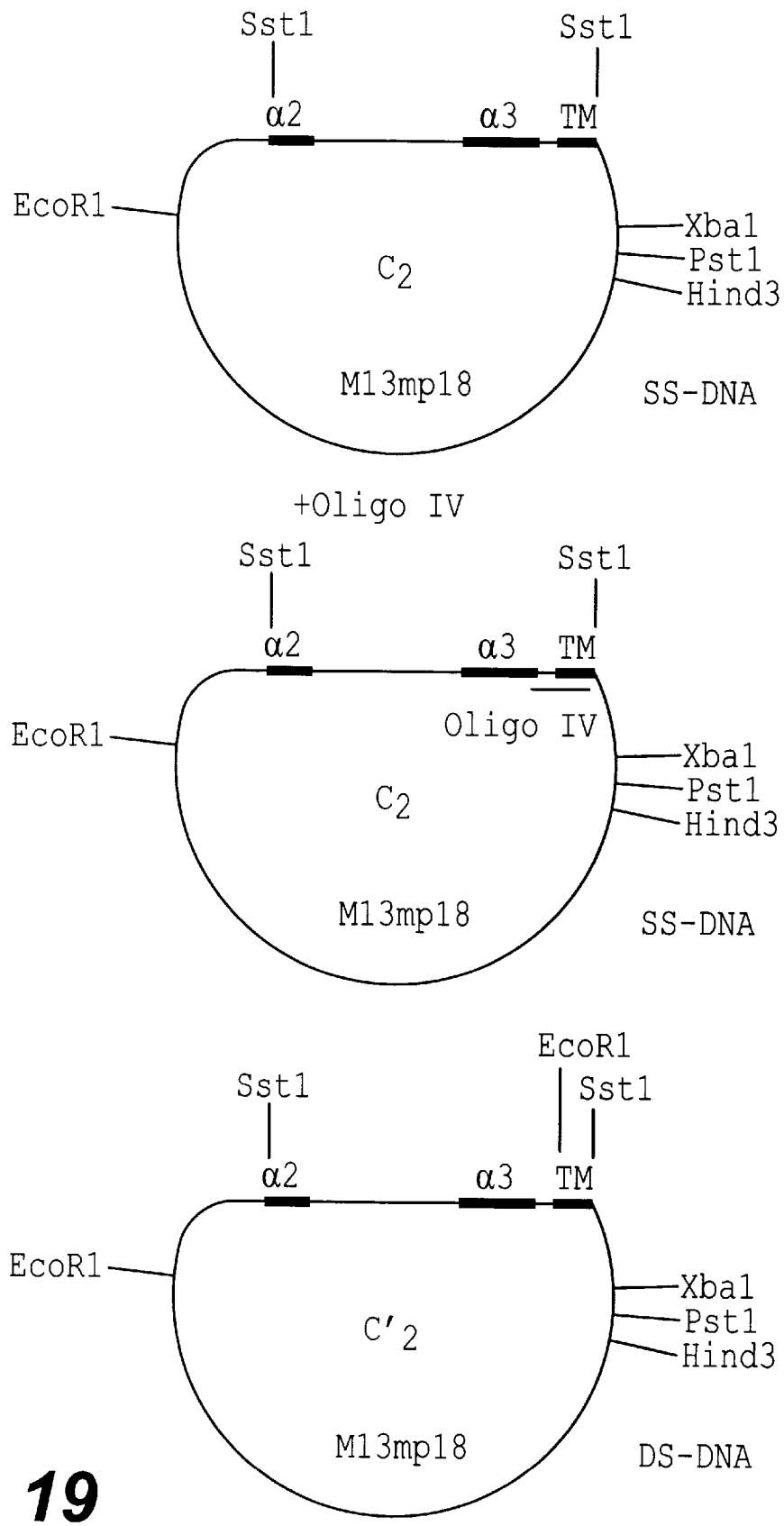
FIG. 19 diagrams introduction into clone C2 of an EcoRI and an AsuII cleavage site into the TM exon of the HLA B27 gene.
Figure 20:
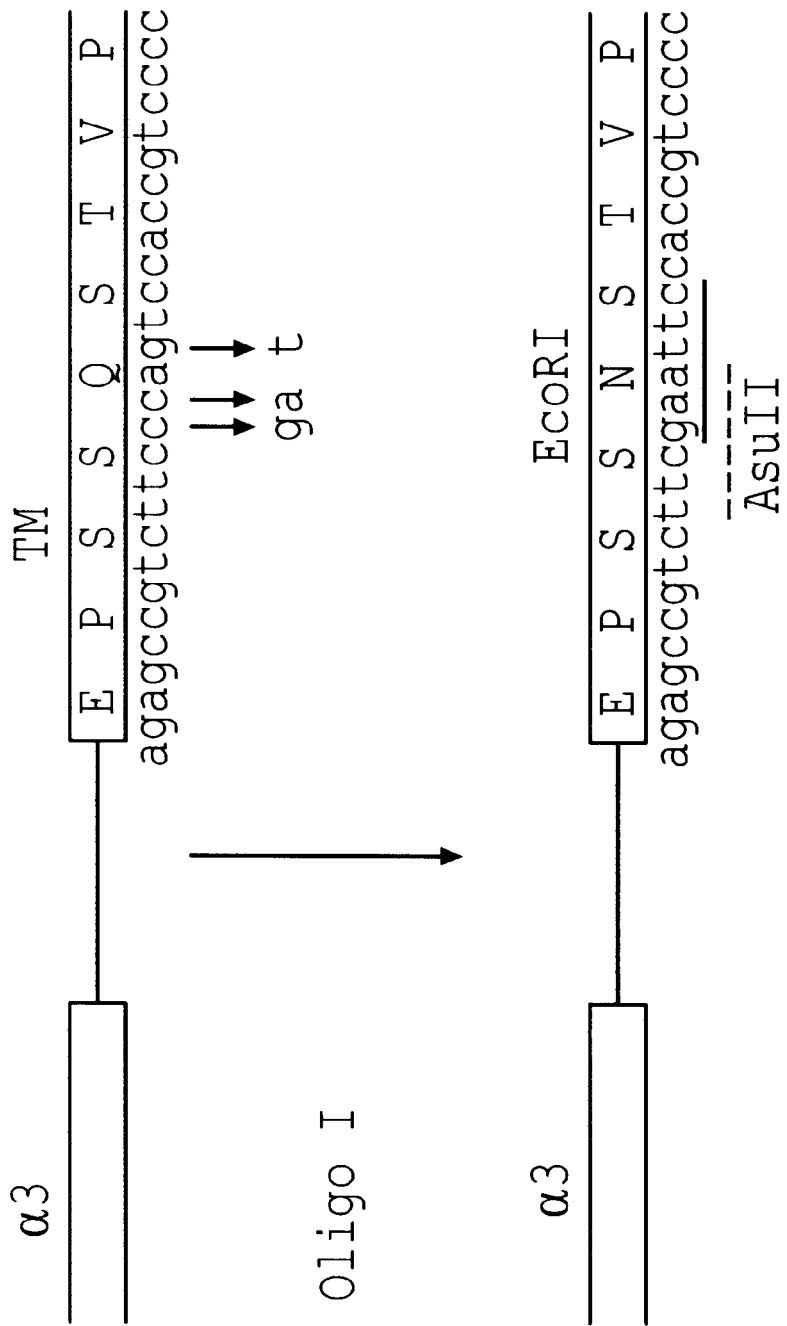
FIG. 20 shows the mutation in clone C2 of amino acid 279 from glutamine into asparagine.

Single-stranded phages were in turn produced from the M13 clone C2 in the bacterial strain CJ236 and were hybridized with the oligonucleotide IV (oligonucleotide IV=5'GGGGACGGTGGAATTCGAAGACGGCTC3'). The second strand was then synthesized with $T_4$ polymerase, To ligase and dNTP. After transformation into MV 1190 bacteria, the M13 mp18 clone C2' was identified by restriction analysis, and the mutation was verified as correct by nucleotide sequence analysis (FIG. 19). This mutagenesis resulted in an EcoRI and an AsuII cleavage site being introduced into the TM exon of the HLA B27 gene, and in amino acid 279 being converted from glutamine into asparagine (FIG. 20).

Example 15

The plasmid clone with the subfragment B was digested with XbaI, and the resulting XbaI insert (B') was cloned in an XbaI-cleaved pUC 19 plasmid (FIG. 7).

Figure 21:
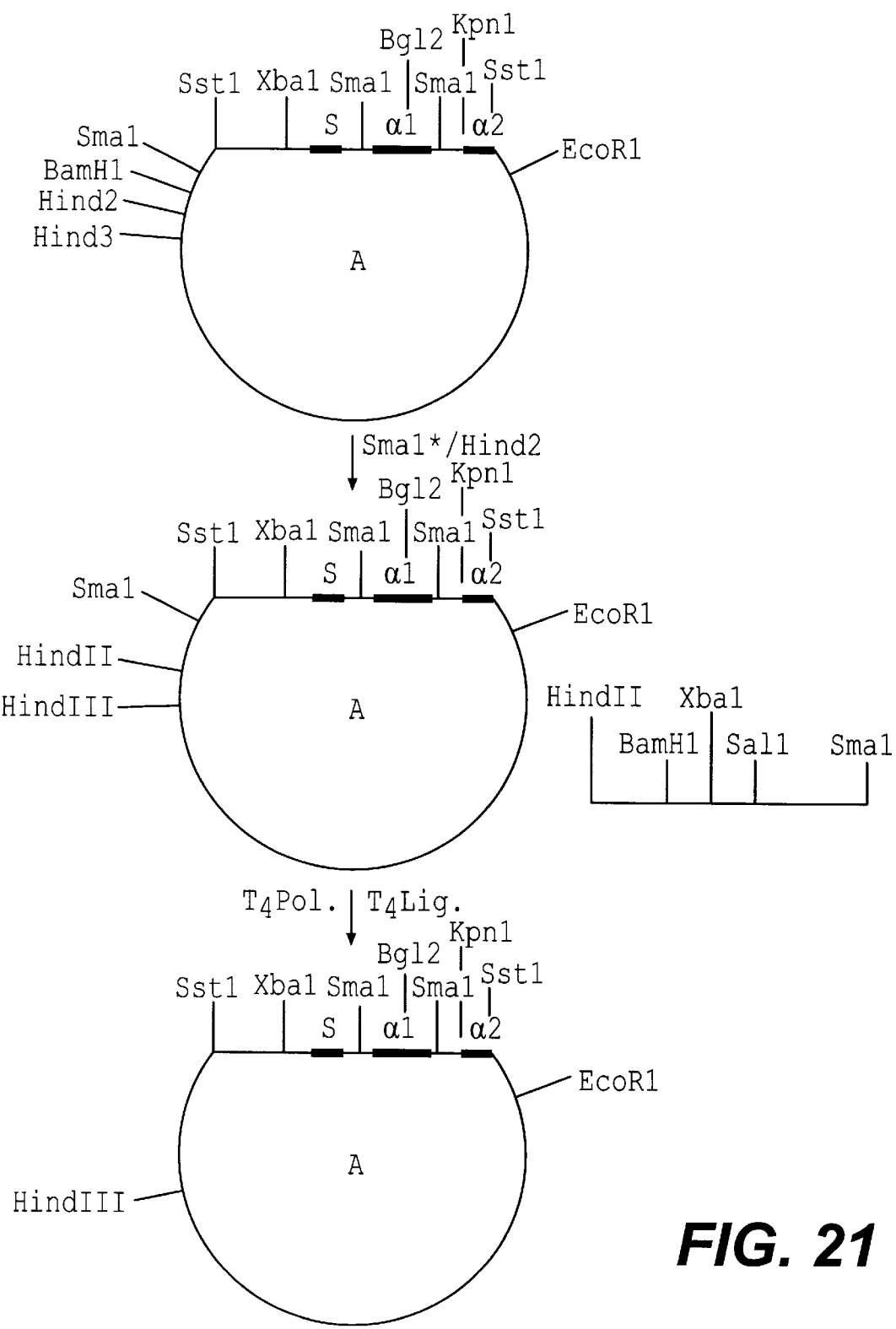
FIG. 21 diagrams the partial deletion of the polylinker from the plasmid clone containing fragment A to yield clone A'.

The plasmid clone with the fragment A was cleaved completely with HindII and partially with SmaI, and religated. Restriction analysis was used to identify the clone A' in which part of the pUC 19 polylinker is deleted (FIG. 21).

Figure 22:
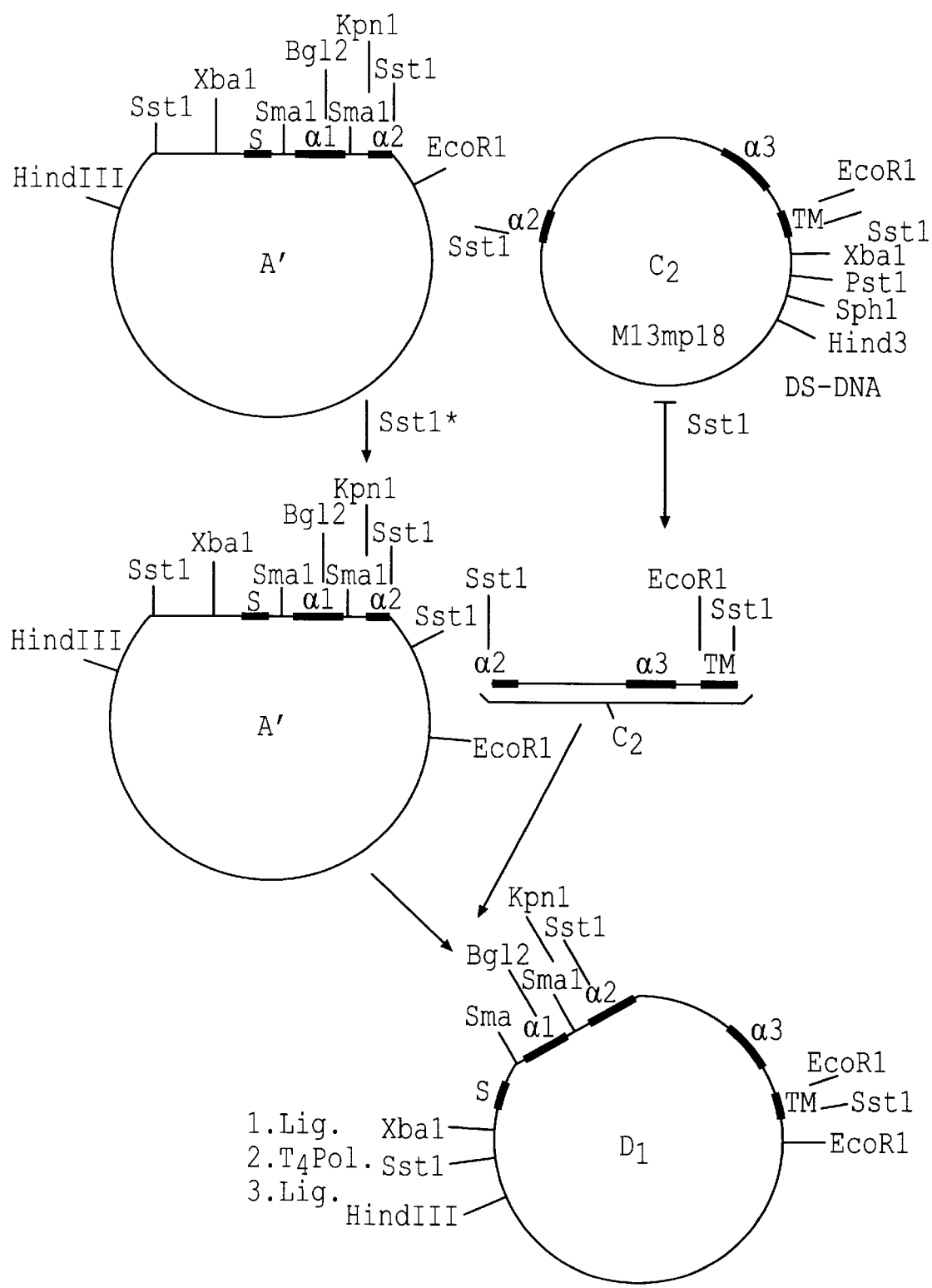
FIG. 22 diagrams ligation of the C$_2$ fragment into plasmid clone A' to yield plasmid D$_1$.

The plasmid clone A' was cleaved partially with SstI and ligated with the C2 fragment generated by an SstI cleavage of the plasmid clone C2 and isolated after fractionation on an agarose gel. Restriction mapping was used to identify the plasmid $D_1$ (FIG. 22) in which the fragment A is connecter to the fragment C2 via the SstI cleavage site in the alpha2 exon. The 5' end of the HLA B27w gene is thus complete.

Construction of the Linker

Two oligonucleotides were synthesized:

oligonucleotide Va:
5' TCGAATTCCG GCGAGGCAGC TCCCGCAGCT GCACCCGCAG CAGCCGCAGC AGGCGGGCAG GTCCAACTGC AGGA 3' oligonucleotide Vb:
5' TCCTGCAGTT GGACCTGCCC GCCTGCTGCG GCT-GCTGCGG GTGCAGCTGC GGGAGCTGCC TCGC-CGGAAT TCGA 3'

Figure 23:
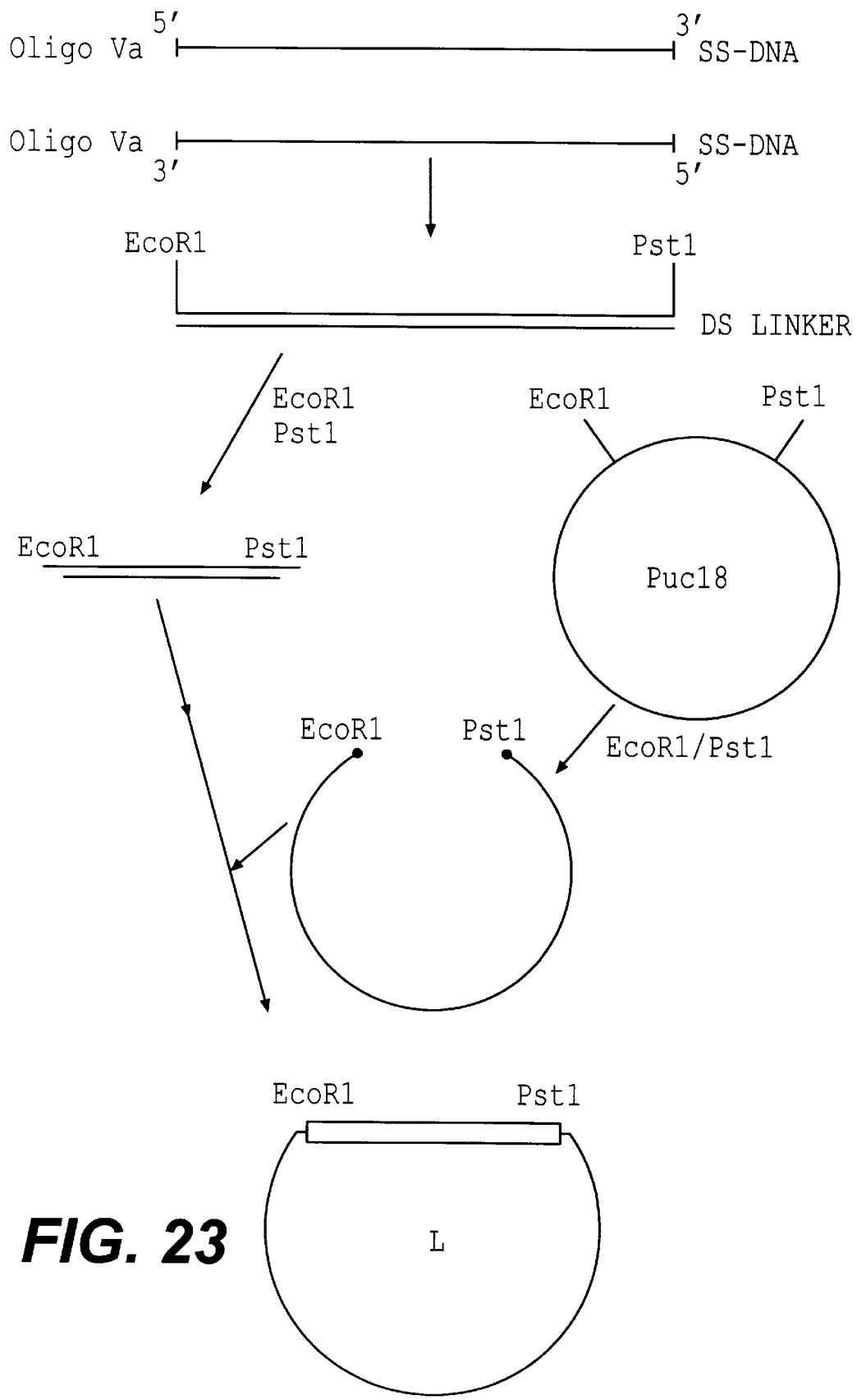
FIG. 23 diagrams cloning of a synthetic DNA formed by hybridization of oligonucleotides Va and Vb into pUC 19 to yield plasmid clone L.

The two oligonucleotides were hybridized together. This resulted in double-stranded DNA fragments with an EcoRI restriction cleavage site at one end and a PstI restriction cleavage site at the other end. These fragments were cleaved with EcoRI and PstI and cloned into an EcoRI- and PstI-cleaved pUC 19 plasmid vector (FIG. 23). The plasmid clone L was identified by restriction analysis and verified by nucleotide sequence analysis.

Figure 24:
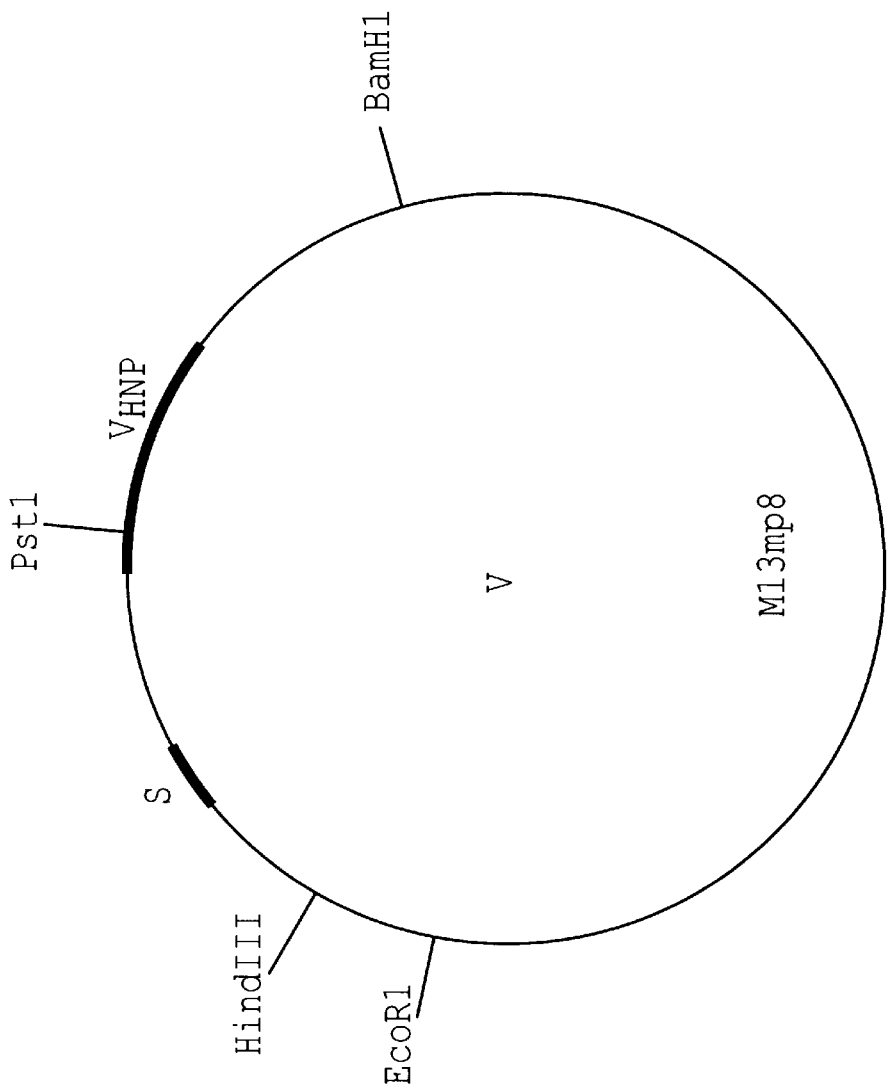
FIG. 24 shows a map of a synthetic immunoglobulin V gene cloned into vector M13 mp8.

The immunoglobulin V gene was synthesized by P. T. Jones et al. (Jones, P. T., Dear, P. H., Foote, J., Neuberger, M. S. Winter, G., Nature 321: 522, (1986)) using oligonucleotides. It contains a PstI restriction cleavage site in the 5' region of the clone and is cloned as HindIII/BamHI fragment in an M13 mp8 vector whose PstI cleavage site had been destroyed by cleavage, removal of the protruding ends and religation (FIG. 24).

II B) Preparation of the mAb C Gene Portion

Example 16

A human IgG3 C gene was isolated from a human gene bank in EMBL3 phages (Frischauf et al., loc. cit. and Seeman et al., loc. cit.) and subcloned into the plasmid vector pUC 19 as a HindIII/SphI fragment 3.1 kb in size (clone 54.1.24) (FIG. 2).

Figure 25:
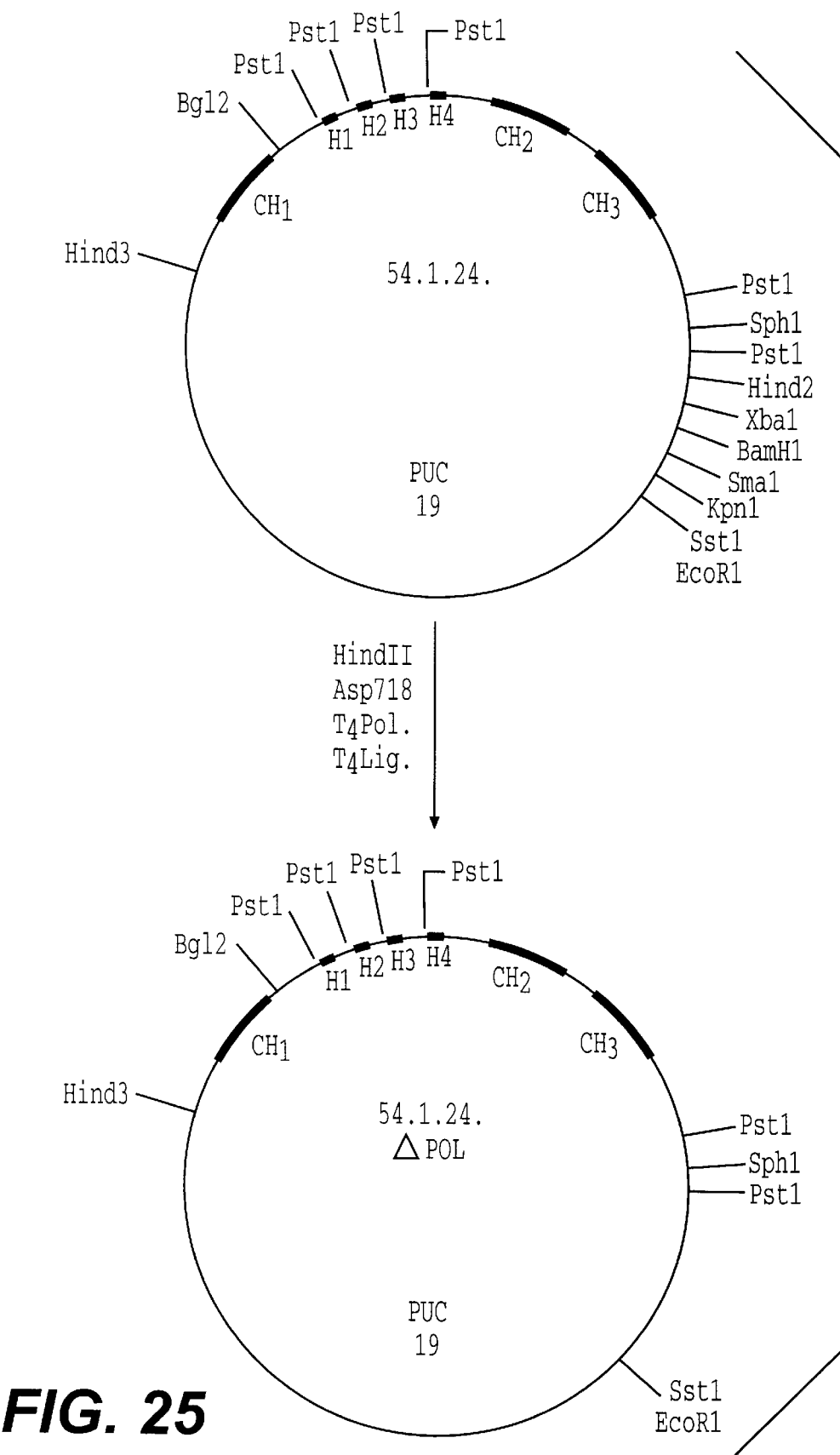
FIG. 25 diagrams removal from clone 54.1.24 of restriction sites 3' of the human IgG3 C gene, to yield clone 54.1.24 Δ Pol.

The plasmid clone 54.1.24 was cleaved with HindII and Asp718, the protruding ends of the Asp718 cleavage site were removed with $T_4$ polymerase and religated with $T_4$ ligase. Restriction analysis and nucleic acid sequence determination were used to identify the clone 54.1.24 Delta Pol which, apart from SphI, PstI, SstI and EcoRI, no longer contains any restriction cleavage sites 3' of the human IgG3 C gene (FIG. 25).

Figure 26:
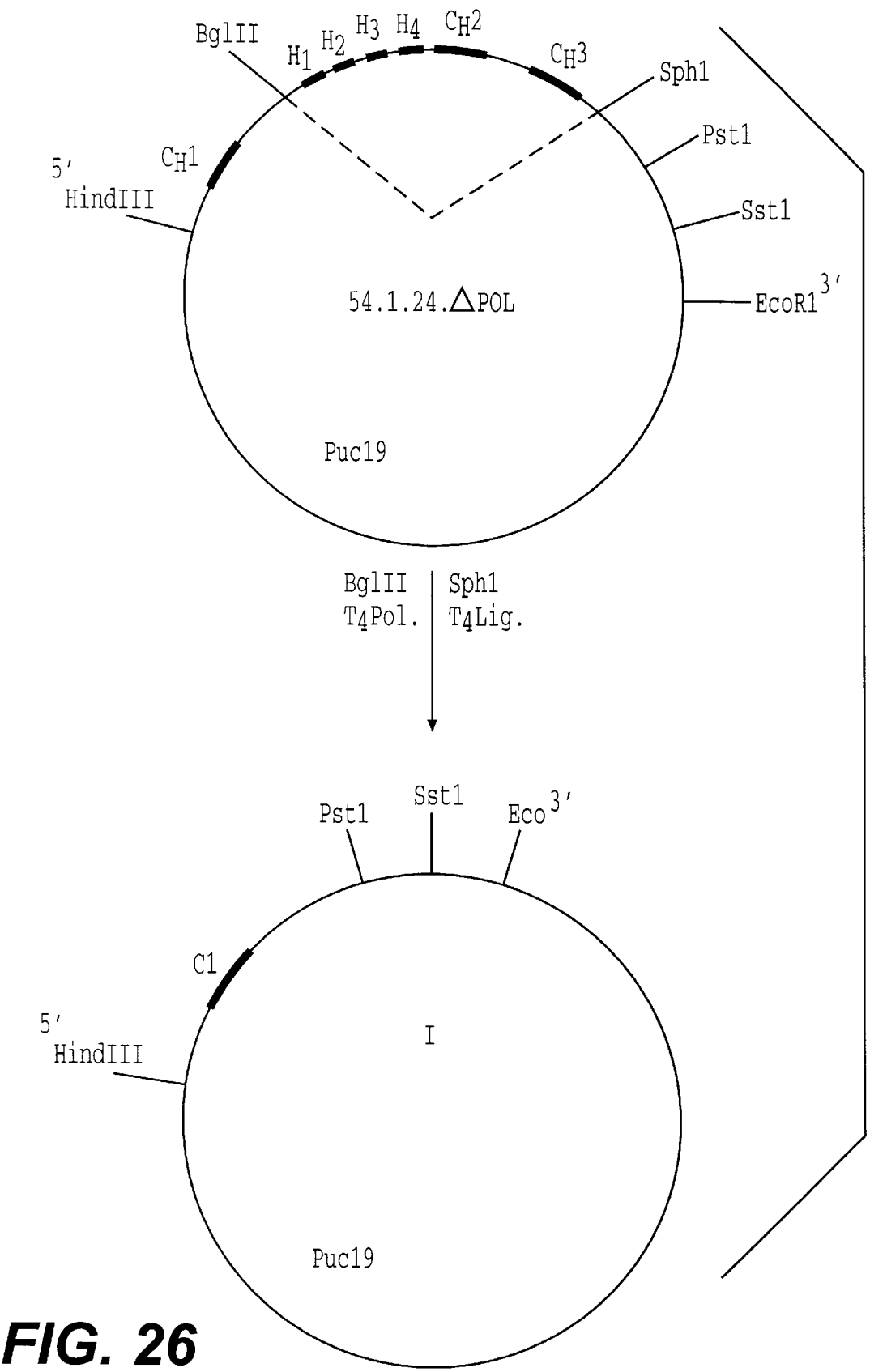
FIG. 26 diagrams digestion of clone 54.1.24 with BglII and SphI to yield clone I, which contains only the CH$_1$ exon of the human IgG3 C gene.

The plasmid clone 54.1.24 Delta Pol was digested with BglII and SphI. The protruding ends were removed with $T_4$ polymerase and religated with $T_4$ ligase. Restriction analysis and nucleic acid sequence determination were used to identify the clone I which now contains only the $CH_1$ exon of the human IgG3 C gene (FIG. 26).

Figure 27:
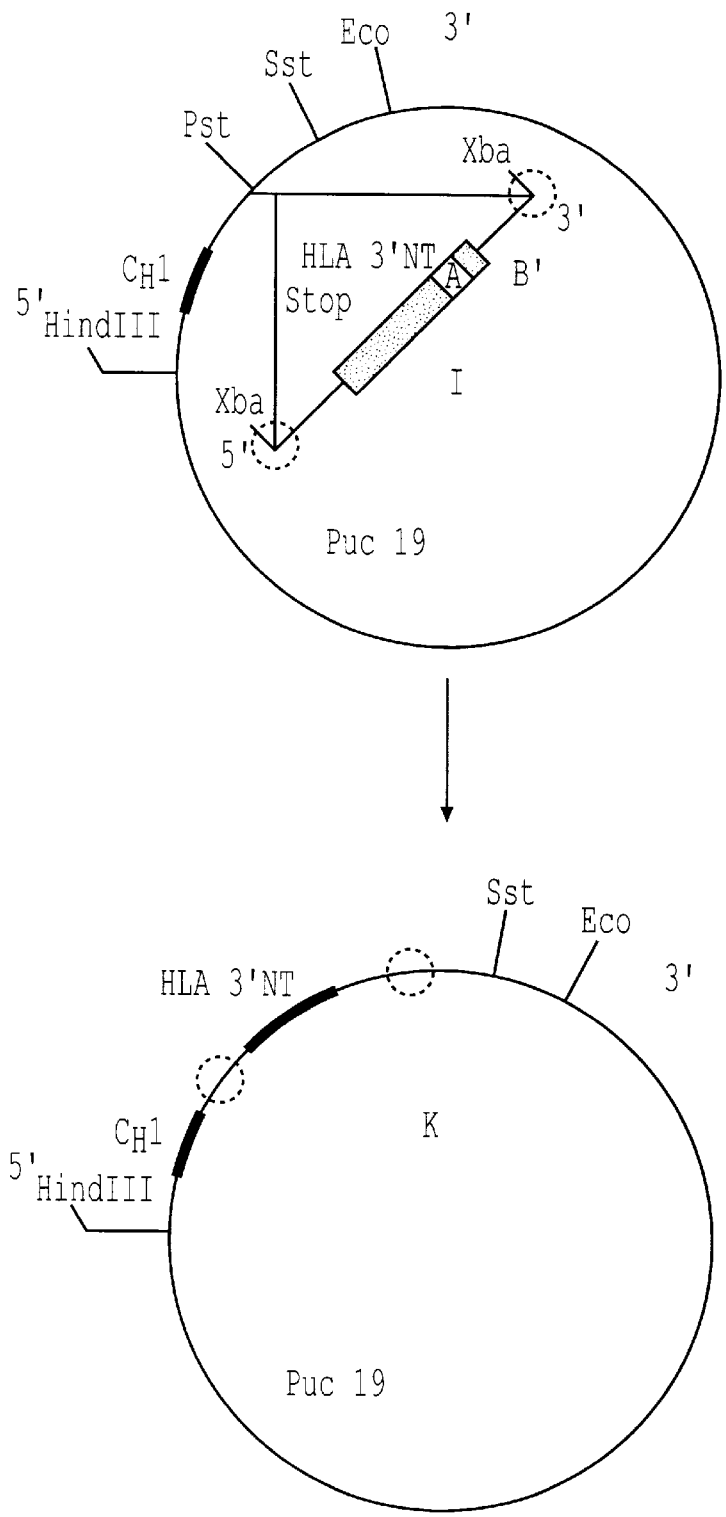
FIG. 27 diagrams cloning of the B' insert into plasmid clone I to yield clone K.

The plasmid clone I was cleaved with PstI, and the protruding ends were removed with $T_4$ polymerase. The B' insert which had been cut with XbaI and filled in with $T_4$ polymerase to give blunt ends was ligated into the resulting blunt ends. Restriction analysis and nucleic acid sequence determination were used to identify the clone K (FIG. 27) which contains a human $IgG_3C_H1$ exon and a 3' end of a HLA class I gene.

Figure 28:
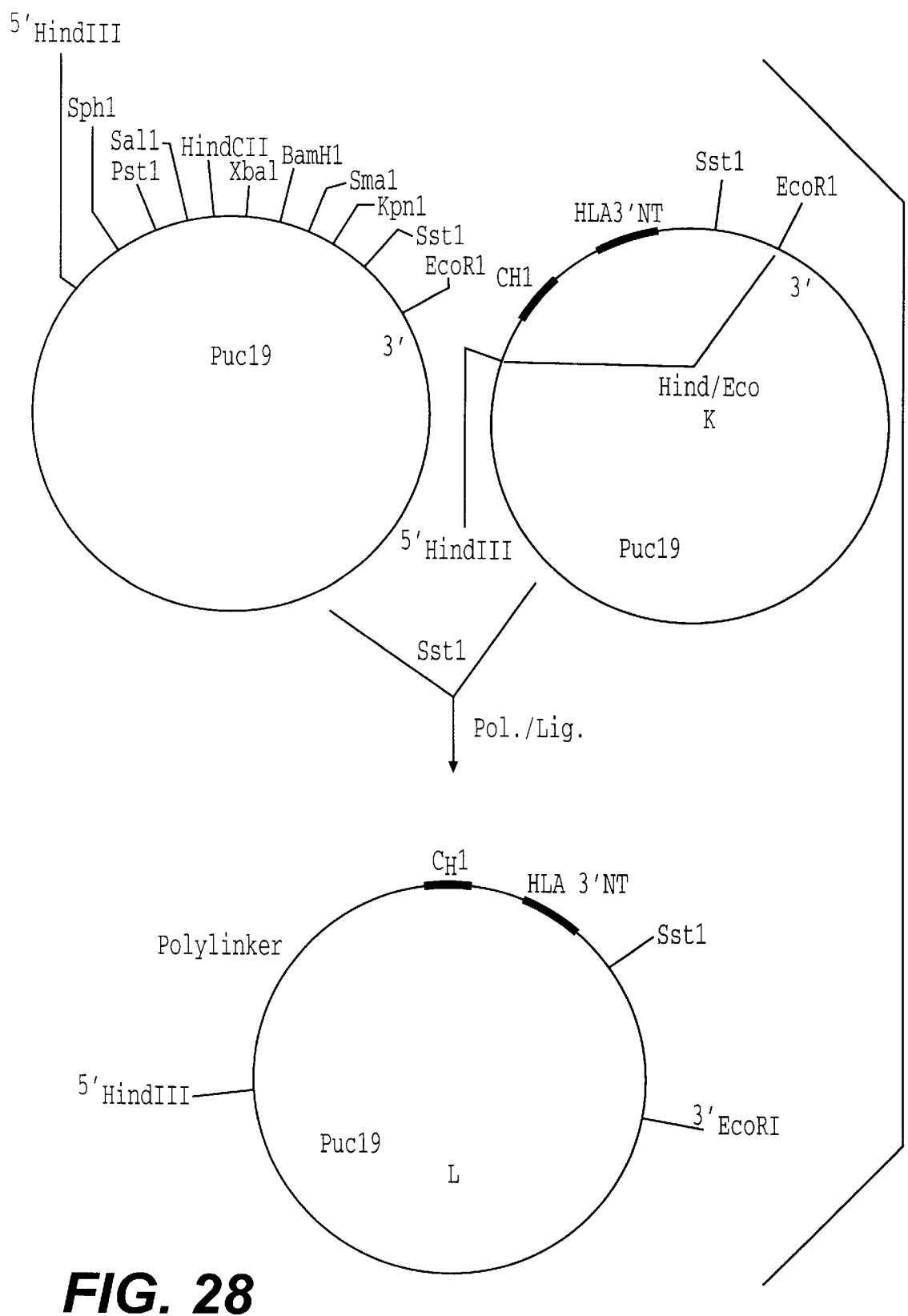
FIG. 28 diagrams ligation of clone K and SstI-cleaved pUC 19 plasmid to yield clone L.

The plasmid clone K was cleaved with HindIII and EcoRI, the protruding ends were removed, and the insert was ligated in an SstI-cleaved pUC 19 plasmid whose ends had likewise been made blunt. The clone L which harbors the polylinker of the pUC 19 vector 5' from the $C_H1$ exon was identified (FIG. 28).

Figure 29:
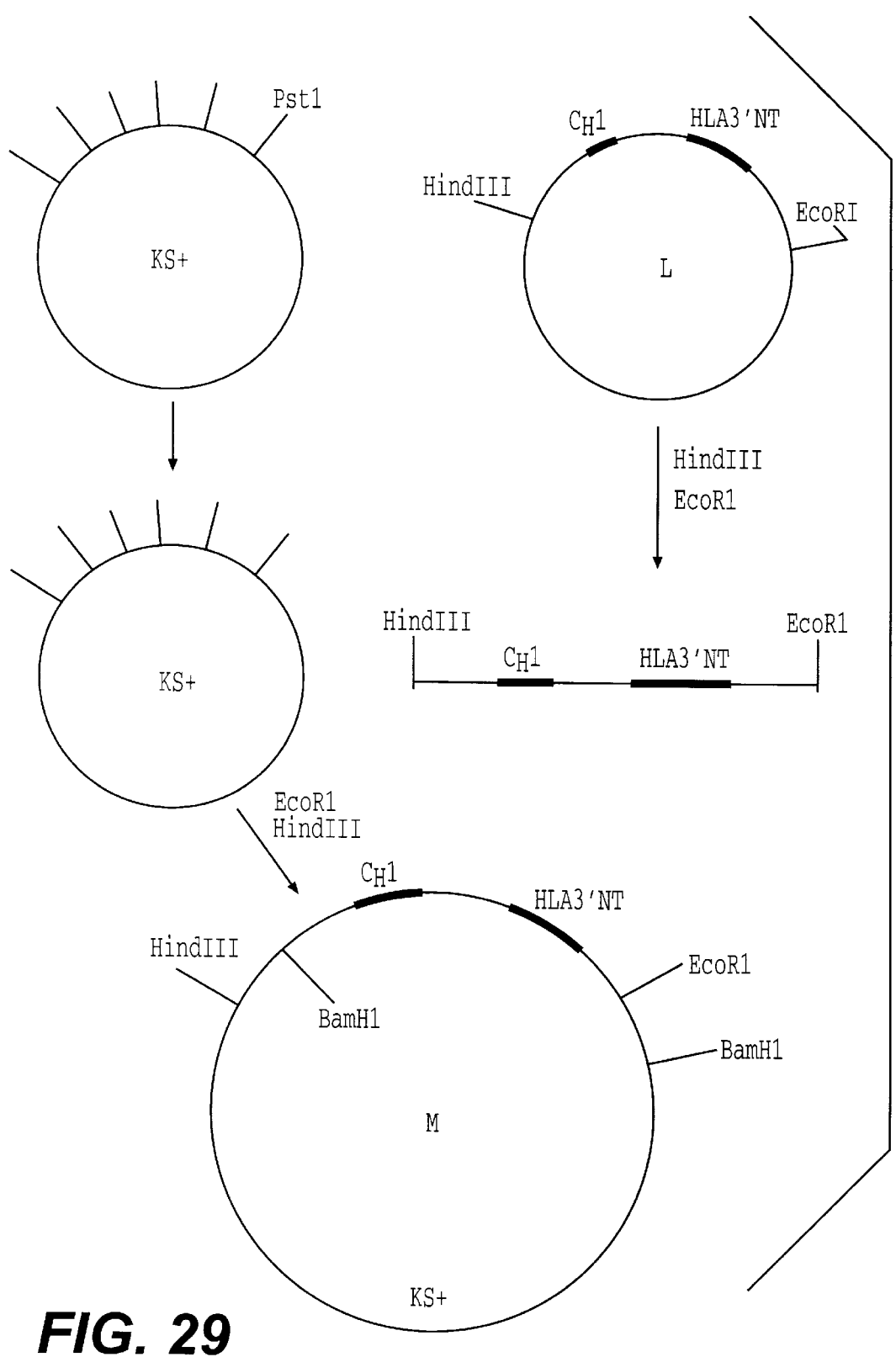
FIG. 29 diagrams cloning of an EcoRI/HindIII fragment from clone L into Bluescript KS$^+$ vector to yield clone M.

The plasmid clone L was cleaved with EcoRI and HindIII, and the insert was purified and ligated into a HindIII- and EcoRI-cleaved KS$^+$ vector (Stratagene; Bluescript Exo/Mung DNA Sequencing System) whose PstI cleavage site had previously been destroyed by cleavage with PstI, $T_4$ polymerase treatment and religation. The clone M, from which it is possible to cut out the human $C_H1$ exon with the HLA class I 3' end by a Bam HI cleavage, was identified (FIG. 29).

Example 17

Figure 30:
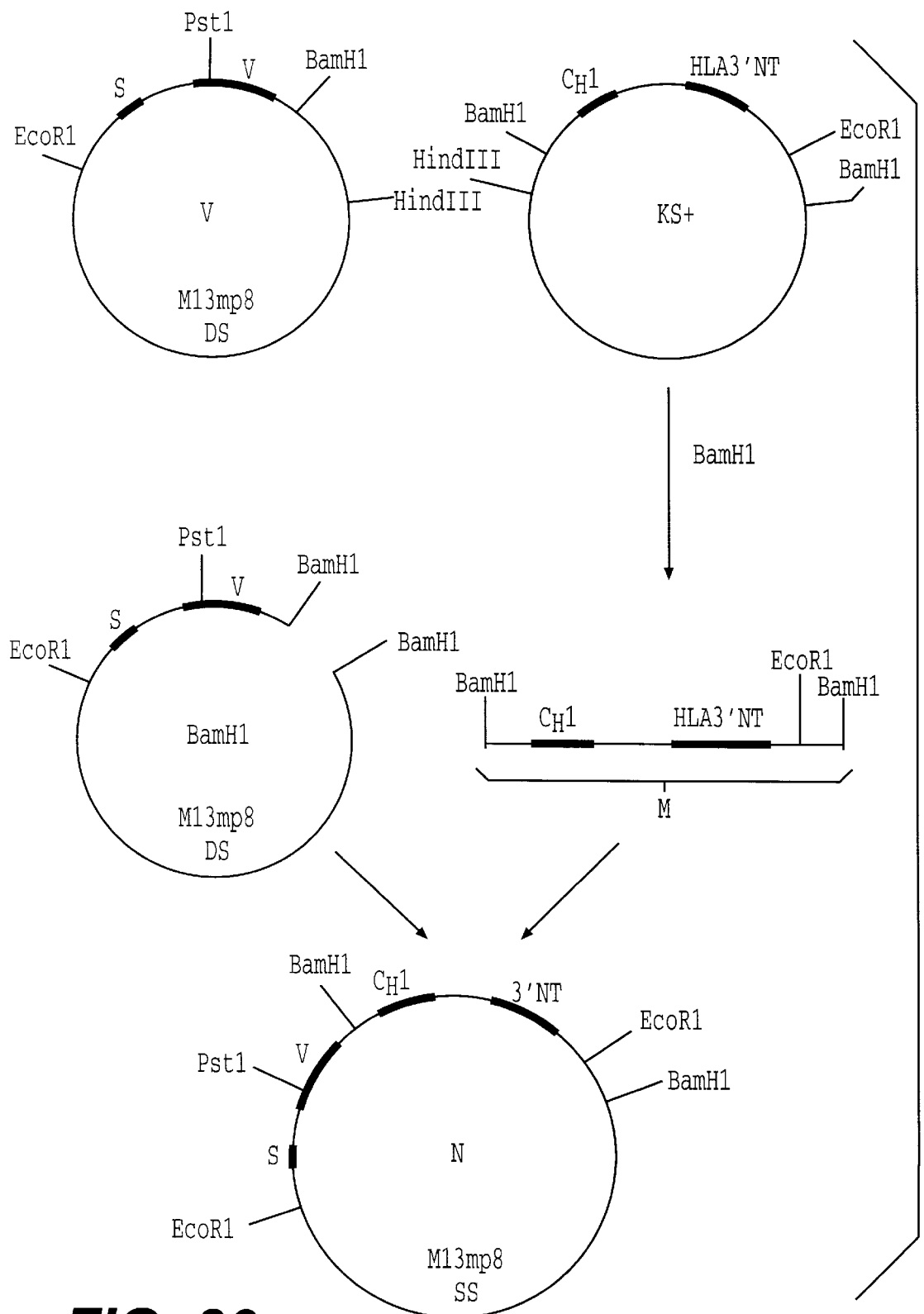
FIG. 30 diagrams ligation of insert M from clone KS+ into M13 mp8 clone V to yield M13 clone N, which contains an intact IgG$_3$ gene.

Double-stranded DNA was prepared from the M13 mp8 clone V and cleaved with BamHI. The KS$^+$ clone M was cleaved with BamHI, and the insert M was purified. The M fragment was ligated into the BamHI-cleaved clone V, and nucleic acid sequence determination was used to identify the M13 clone N which contains an intact IgG3 gene (FIG. 30).

Figure 31:
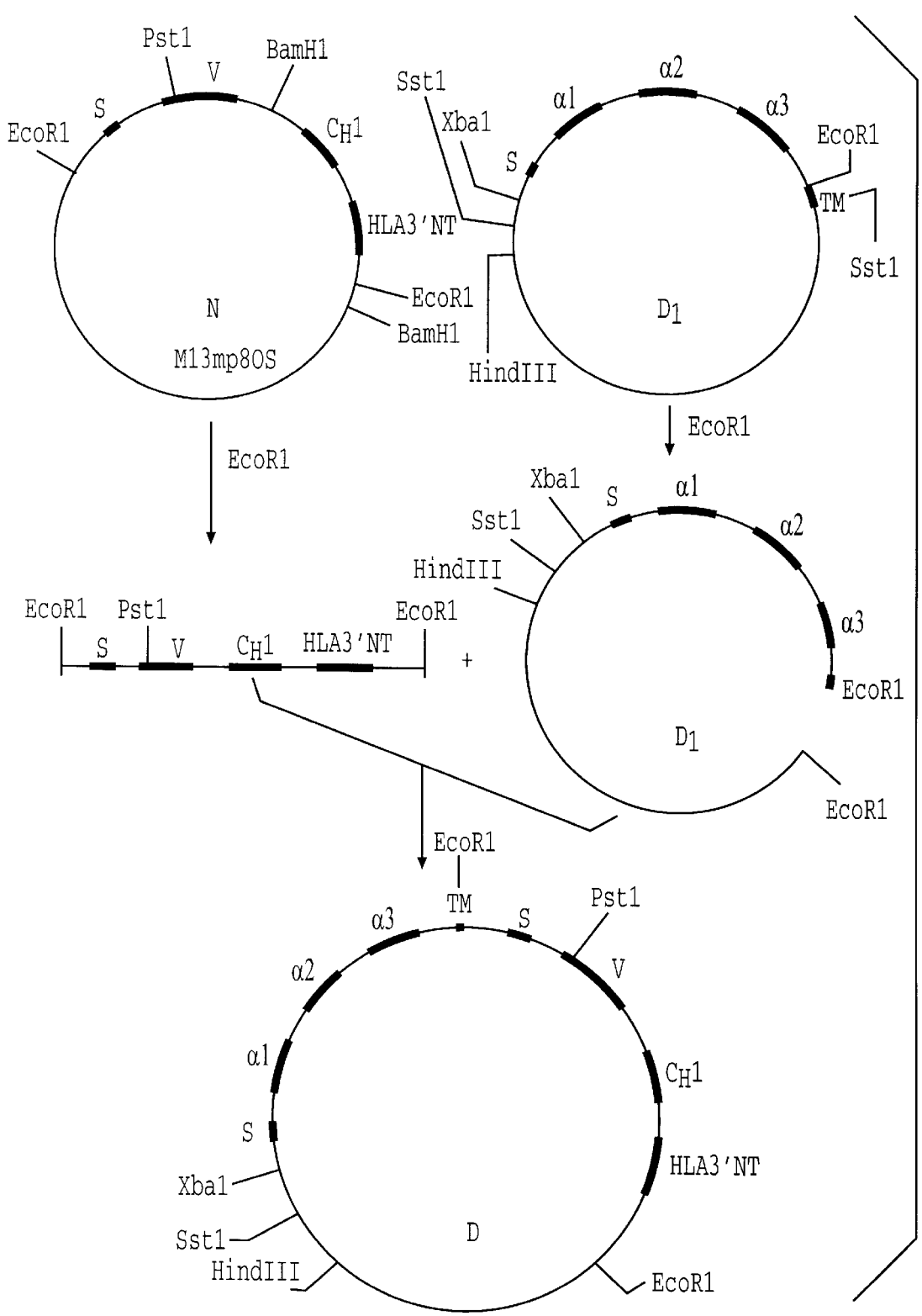
FIG. 31 diagrams the ligation of an EcoRI fragment from clone N into EcoRI-digested plasmid clone D$_1$ to yield phage clone O.

Double-stranded DNA was prepared from the M13 clone N and was cleaved with EcoRI, and the insert was purified. The plasmid clone $D_1$ was cleaved with EcoRI and ligated with the fragment N. The phage clone O in which the fragment N is cloned in the correct orientation into the clone $D_1$ was isolated (FIG. 31).

Figure 32:
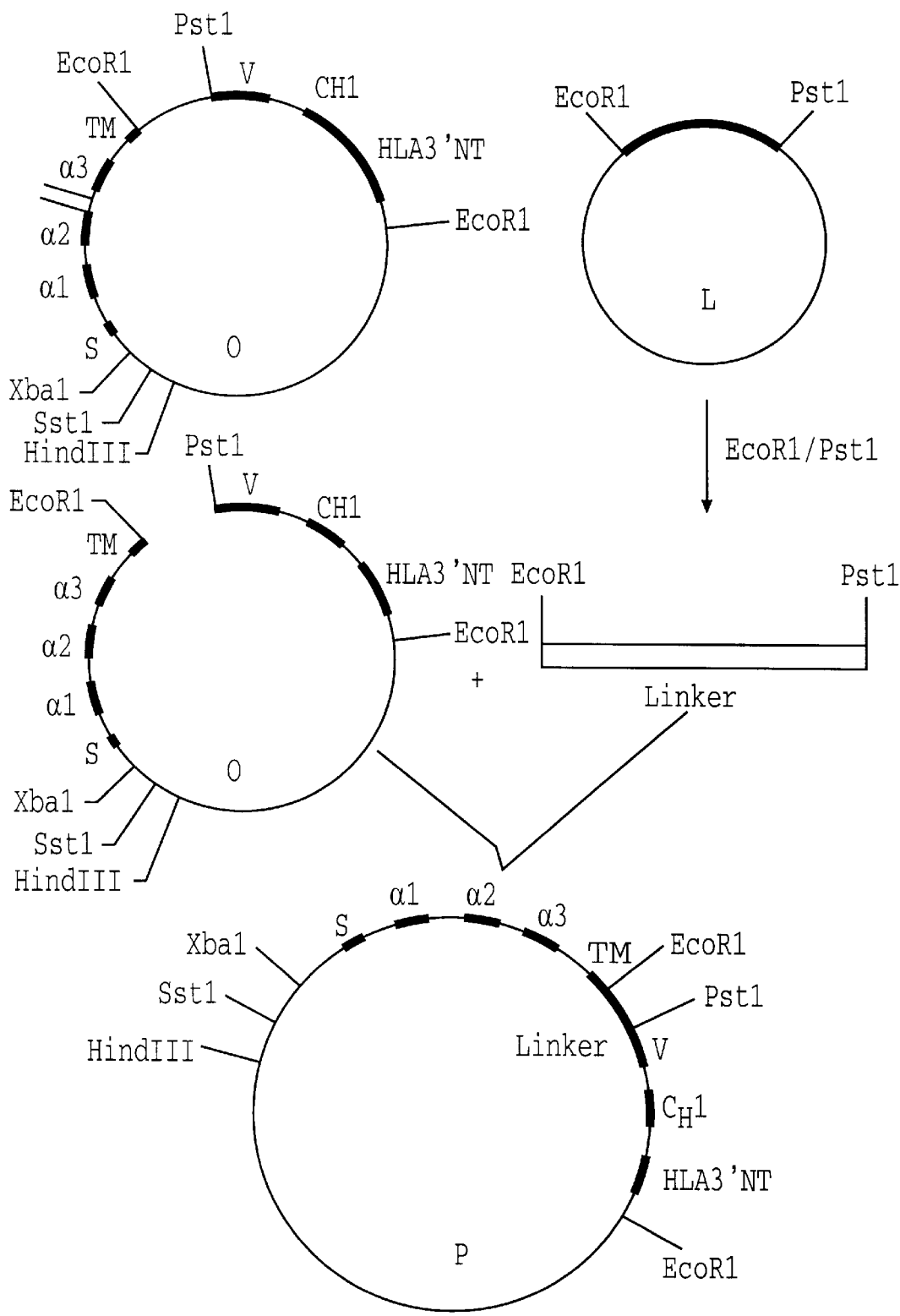
FIG. 32 diagrams ligation of the linker fragment cut out of plasmid L with EcoRI and PstI into plasmid O to yield plasmid P.
Figure 33:
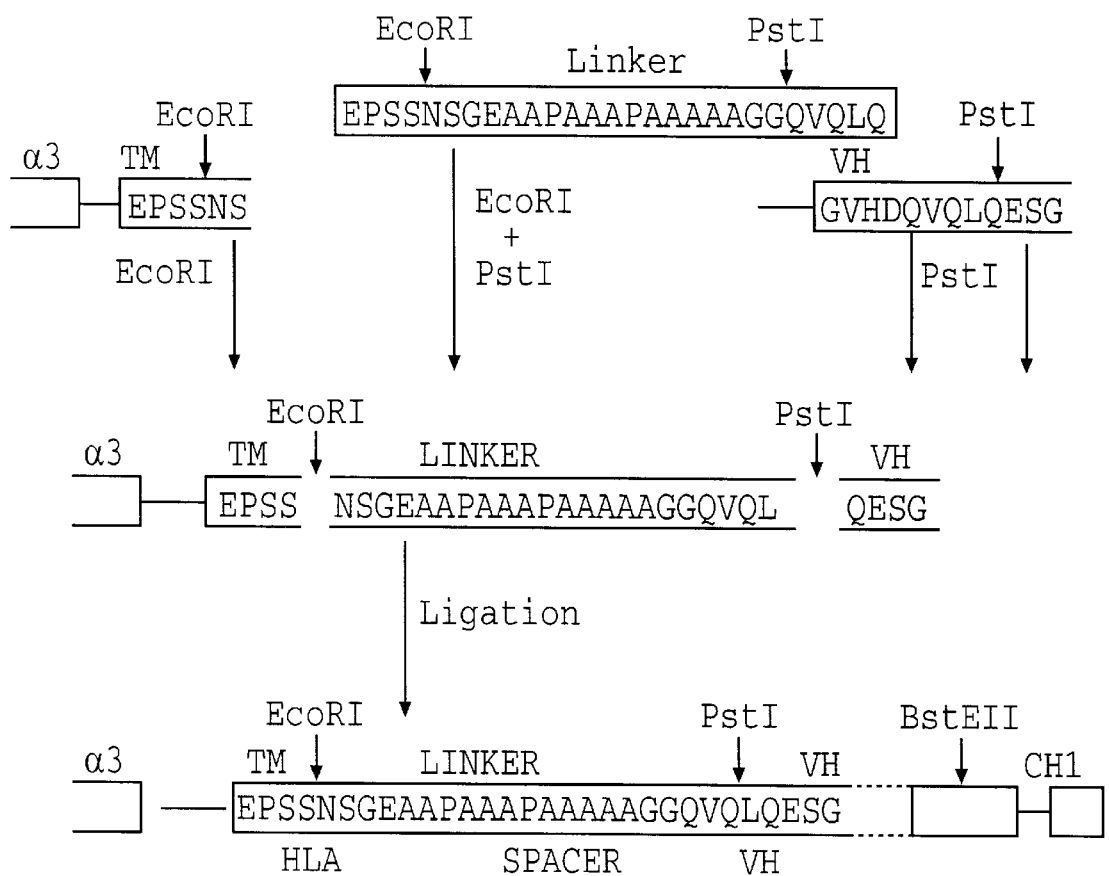
FIG. 33 shows the construction of plasmid P.

The plasmid clone O was subjected to a complete PstI cleavage and partial EcoRI cleavage and ligated with the linker fragment cut out of the plasmid vector L with EcoRI and PstI. The plasmid clone P contains the complete HLA B27w mAb fusion gene (FIG. 32, FIG. 33). This fusion gene can be expressed and secreted in human cells alone or in mouse cells together with the human beta$_2$ microglobulin gene if the expressing cells also contain an immunoglobulin light chain.

Key to FIG. 1
  alpha 1, alpha 2 and alpha 3 denote the domains of the class I MHC antigen chain. The arrows point to the alpha helices which carry the allodeterminants. CM is meant to represent the cell membrane, and C the cell.

Key to FIG. 2 et seq.
  EcoRI etc. represents the cleavage with the particular restriction endonuclease or represents the corresponding cleavage site. etc. denotes a restriction cleavage site destroyed by religation after filling-in.
  TM denotes the transmembrane region.
3'NT denotes 3' non-translated IgH p/E denotes the immunoglobulin heavy chain promoter/enhancer
* denotes: incomplete digestion
DS-DNA denotes: double-stranded DNA
SS-DNA denotes: single-stranded DNA
Key to FIG. 34:
s.CTL denotes: syngeneic cytotoxic T lymphocyte
TcR denotes: T-cell receptor
a.MHC class I denotes: allogenic MHC class I antigen
t.a.a. denotes: tumor-associated antigen
s.t.c. denotes: syngeneic tumor cell

What is claimed is:

1. An antigenic construct comprising a cytotoxic T cell stimulating allogenic major histocompatibility complex (MHC) class I antigen linked at its C-terminal or N-terminal end to a target-cell-specific carrier molecule, wherein said construct can be used to activate cytotoxic T cells.

2. An antigenic construct as claimed in claim 1, wherein one allogenic MHC class I antigen is linked to one target-cell-specific carrier molecule.

3. An antigenic construct as claimed in claim 1, wherein said allogenic MHC class I antigen is HLA B27w or HLA B27k.

4. An antigenic construct as claimed in claim 1, wherein said allogenic MHC class I antigen is covalently bonded to said target-cell-specific carrier molecule.

5. An antigenic construct as claimed in claim 1 prepared by fusion of the DNAs coding for said allogenic MHC class I antigen and said target-cell-specific carrier molecule.

6. An antigenic construct as claimed in claim 1 wherein said target cell-specific carrier molecule is selected from the group consisting of monoclonal antibodies, polyclonal antibodies, or other molecules which bind to receptors on target cells.

7. An antigenic construct as claimed in claim 6, wherein the target-cell-specific carrier molecule is a monoclonal antibody.

8. An antigenic construct as claimed in claim 7, wherein at least one heavy chain constant region of the monoclonal antibody has been partially deleted.

9. An antigenic construct comprising a cytotoxic T cell stimulating allogenic major histocompatibility complex (MHC) class I antigen linked at its N-terminal end to a target-cell-specific carrier molecule.

10. An antigenic construct comprising a cytotoxic T cell stimulating allogenic major histocompatibility complex (MHC) class I antigen linked at its C-terminal end to a target-cell-specific carrier molecule.

* * * * *